United States Patent [19]

Bauman et al.

[11] Patent Number: 5,602,246
[45] Date of Patent: Feb. 11, 1997

[54] PROCESS FOR THE PREPARATION OF FLUDARABINE OR FLUDARABINE PHOSPHATE FROM GUANOSINE

[75] Inventors: John G. Bauman, Alameda; Randolph C. Wirsching, Livermore, both of Calif.

[73] Assignee: Schering Aktiengesellschaft, Berlin, Germany

[21] Appl. No.: 981,114

[22] Filed: Nov. 25, 1992

[51] Int. Cl.$^6$ ............................ C07H 1/00; C07H 19/167; C07H 19/20

[52] U.S. Cl. .................... 536/55.3; 536/26.3; 536/27.61; 536/27.63

[58] Field of Search ......................... 536/27.61, 27.63, 536/55.3, 26.3

[56] References Cited

U.S. PATENT DOCUMENTS

| | | | |
|---|---|---|---|
| 2,719,843 | 10/1955 | Davoll et al. | 536/27.11 |
| 3,074,929 | 1/1963 | Hitchings et al. | 536/27.8 |
| 3,074,930 | 1/1963 | Hitchings et al. | 536/27.21 |
| 3,309,358 | 3/1967 | Hanze | 536/26.5 |
| 3,314,938 | 4/1967 | Kawashima et al. | 536/27.21 |
| 3,541,079 | 11/1970 | Schramm et al. | 536/27.11 |
| 4,038,479 | 7/1977 | Elion et al. | 536/27.61 |
| 4,188,378 | 2/1980 | Montgomery | 536/27.4 |
| 4,210,745 | 7/1980 | Montgomery | 536/27.11 |
| 4,357,324 | 11/1982 | Montgomery et al. | 514/45 |
| 4,594,350 | 6/1986 | Vince | 514/261 |
| 4,760,137 | 7/1988 | Robins et al. | 536/27.11 |
| 4,908,441 | 3/1990 | Cook et al. | 536/26.7 |
| 4,918,179 | 4/1990 | Watanabe et al. | 536/27.4 |
| 4,921,950 | 5/1990 | Wilson | 536/28.54 |

FOREIGN PATENT DOCUMENTS

| | | |
|---|---|---|
| 91/08215 | 6/1991 | WIPO. |
| 92/00312 | 1/1992 | WIPO. |

OTHER PUBLICATIONS

Bridson et al., J.C.S. Chem. Commun., pp. 791–792 (1977).
Higuchi et al., Anal. Chem., 28:1022 (1956).
Sproat et al., Nucleic Acids Research, 18:41–49 (1990).
Montgomery et al., J. Am. Chem. Soc., 82:463–468 (1960).
Montgomery et al., J. Med. Chem., 12:498–504 (1969).
Robins et al., Can J. Chem., 59:2608–2611 (1981).
Robins et al., Can. J. Chem. 59:2601–2607 (1981).
Timoshchuk et al., Pharmaceutical Chem. Journal, 19:259–261 (1985).
Zhang et al., Tetrahedron Letters, vol. 33, No. 9, pp. 1177–1180 (1992).

Montgomery et al., J. Med. Chem., 35:397–401 (1992).
Vorbrüggen et al., Liebigs Ann. Chem., pp. 745–761 (1976).
Hansske et al., Tetrahedron, vol. 40, No. 1, pp. 125–135 (1984).
Montgomery et al., J. Org. Chem., 33:432–435 (1968).
Olah et al., J. Org. Chem., vol. 44, No. 22, pp. 3872–3881 (1979).
Ishido et al., J. Chem. Soc. P1, pp. 2–88–2098 (1979).
Ballestri et al., J. Org. Chem., 56:678–683 (1991).
Morisawa et al., Tetrahedron Letters, vol. 21, pp. 479–482 (1980).
Huang et al., J. Med. Chem., 27:800–802 (1984).
Christensen et al., J. Med. Chem., vol. 15, No. 7, pp. 735–739 (1972).
Huang et al., Biochemical Pharmacology, vol. 30, No. 19, pp. 2663–2671 (1981).
Keller et al., J. Org. Chem., 32:1644–1646 (1967).
Nucleic Acid Chemistry, Part III, pp. 156–161, L. B. Townsend, ed., John Wiley & Sons, New York, NY (1986).
Robins et al., Can. J. Chem., 59:3360–3364 (1981).
Samano et al., J. Org. Chem., 55:5186–5188 (1990).
Jiang et al., Nucleosides & Nucleotides, 7(3):271–294 (1988).
Fukukawa et al., Chem. Phamr. Bull. 31(5):1582–1592 (1983).
*Nucleosides, Nucleotides, and Their Biological Applications*, pp. 279–295 J. L. Rideout et al., eds., Academic Press (1983).
Sakairi et al., Nucleosides & Nucleotides, 2(3):221–229 (1983).
Secrist et al., J. Med. Chem., 31:405–410 (1988).
Markiewicz et al., Tetrahedron Lett., vol. 29, No. 13, pp. 1561–1564 (1988).
Ishido et al., J. Chem. Soc., P1, pp. 563–573 (1980).
Matsuda, Synthesis, pp. 385–386 (May 1986).
Blakely et al., Adv. Exp. Med. Biol., 195B:589–593 (1986).

*Primary Examiner*—Gary L. Kunz
*Attorney, Agent, or Firm*—Millen, White, Zelano & Branigan, P.C.

[57] ABSTRACT

A process for the production of fludarabine or fludarabine phosphate is provided, wherein the nucleoside guanosine or a suitable derivative is employed as the starting material. The guanosine starting material is subjected to (a) conversion of the 6-keto group into a 6-amino group, (b) conversion of the 2-amino group to a 2-fluoro group, and (c) conversion of the ribofuranosyl moiety to an arabinofuranosyl moiety. Steps (a), (b), and (c) can be performed individually or concomitantly and in any sequence.

34 Claims, 7 Drawing Sheets

PROCESS FOR THE PREPARATION OF FLUDARABINE OR FLUDARABINE PHOSPHATE FROM GUANOSINE

BACKGROUND OF THE INVENTION

The invention relates to methods of producing fludarabine or fludarabine phosphate. The invention also relates to intermediates useful in the production of fludarabine or fludarabine phosphate, as well as methods of producing such intermediates.

Fludarabine phosphate, also known as 9-β-D-arabinofuranosyl-2-fluoroadenine-5'-phosphate, is a prodrug form of the anti-cancer agent, 9-β-D-arabinofuranosyl-2-fluoroadenine, i.e., fludarabine or F-Ara-A. Accordingly, fludarabine phosphate is a chemotherapeutically effective form of the drug and is converted to the parent drug in vivo.

U.S. Pat. No. 4,210,745 discloses a method of synthesizing the anti-cancer agent, and U.S. Pat. No. 4,357,324 teaches phosphorylation of the cancer agent to yield the prodrug fludarabine phosphate. World patent application WO 91/08215 discloses a related method for the synthesis of fludarabine phosphate. In summary, fludarabine and fludarabine phosphate are commonly made by the following process:

(a) Acylation: 2,6-diaminopurine (also referred to as 2-aminoadenine) in a mixture of pyridine and a carboxylic acid anhydride is refluxed to yield a 2,6-diacylamidopurine, whereby the amino groups are protected with acyl groups;

(b) Coupling: 2,3,5-tri-O-benzyl-1-O-p-nitrobenzoyl-D-arabinofuranose (TBNA) is converted to the corresponding chlorosugar, 2,3,5-tri-O-benzyl-1-α-chloro-D-arabinofuranose, which is then coupled with the 2,6-diacylamidopurine in a non-polar solvent such as ethylene dichloride and in the presence of a catalyst such as molecular sieves for several days until all of the chlorosugar is consumed or in the presence of a hydrochloric acid acceptor such as diisopropylethylamine, to yield the protected nucleoside 2,6-diacylamido-9-β-D-(2',3',5'-tri-O-benzylarabinofuranosyl)purine;

(c) Deacylation: The protected nucleoside of step (b) is refluxed with methanolic sodium methoxide to remove the acyl groups, yielding the O-protected nucleoside 2-amino-9-β-D-(2',3',5'-tri-O-benzylarabinofuranosyl)adenine;

(d) Diazotization/Fluorination: The O-protected nucleoside of step (c) undergoes diazotization and fluorination by reaction with sodium nitrite and fluoboric acid in a tetrahydrofuran-fluoboric acid (THF-HBF$_4$) system to yield 2-fluoro-9-β-D-(2',3',5'-tri-O-benzylarabinofuranosyl)adenine;

(e) Debenzylation: The product from step (d) is treated with boron trichloride or with hydrogen and palladium chloride to remove the benzyl protecting groups, yielding 9-β-D-arabinofuranosyl-2-fluoroadenine, the parent drug; or (f) Phosphorylation: The product from step (e) is mixed with phosphorous oxychloride in an alkyl phosphate such as triethylphosphate, or trimethylphosphate, followed by hydrolysis in water to yield the prodrug 9-β-D-arabinofuranosyl-2-fluoroadenine-5'-phosphate or fludarabine phosphate.

One of the disadvantages of this process is that the protected sugar (TBNA) used in step (b) is very costly and has limited commercial availability. Since the diazotization/fluorination reaction in step (d) has a relatively low yield, the overall yield of fludarabine or fludarabine phosphate from this costly material is undesirably low. Therefore, it would be preferable to provide a process which avoids the use of the costly protected sugar. In addition, since the coupling reaction may be difficult to scale-up, and is not completely stereoselective, it would be desirable to have a process which does not require a coupling step of this type.

Although the yield and reliability of the coupling reaction are improved and the reaction time is decreased substantially by using the modified procedure described in WO 91/08215, this modified procedure requires the use of a more complex anhydride, which is not commercially available. This adds an additional step to the process, because the anhydride itself must be prepared.

The 2,6-diaminopurine starting material also is expensive and has limited commercial availability. Therefore, it would be desirable to provide a process which does not require this starting material.

A further disadvantage of the prior art process, as indicated above, is the low yields of 2-fluoro-adenosine compound from the diazotization/fluorination step using the THF-HBF$_4$ system. Therefore, it would be advantageous to provide a process wherein the 2-fluoro group is introduced more efficiently.

SUMMARY OF THE INVENTION

An object of the invention is to provide a novel process for the synthesis of fludarabine or fludarabine phosphate. More particularly, an object of the invention is to provide a novel process for the synthesis of fludarabine or fludarabine phosphate which does not exhibit the disadvantages associated with the above-described prior art process and which employs a nucleoside as the starting material.

Upon further study of the specification and appended claims, further objects and advantages of this invention will become apparent to those skilled in the art.

These objects are achieved by a process for the production of fludarabine, wherein guanosine is subjected to:

(a) conversion of the 6-keto group into a 6-amino group, (b) conversion of the 2-amino group to a 2-fluoro group, and (c) conversion of the ribofuranosyl moiety to an arabinofuranosyl moiety. Steps (a), (b), and (c) can be performed individually or concomitantly and in any sequence.

Furthermore, certain aspects of the invention are particularly preferred. These include:

(a) conversion of the ribofuranosyl sugar moiety to the arabinofuranosyl moiety via an intermediate having a 3',5'-disiloxane bridge, a 2'-oxo group and a 2-fluoro group;

(b) production and use of 3',5'-diacyl-2'-OSO$_2$R$^2$-2-fluoro intermediate during sugar conversion;

(c) production and use of 3',5'-diacetyl-2'-oxo-2-fluoroadenine intermediates during sugar conversion;

(d) halogen exchange converting 6-chloro or 6-bromo compounds to 6-fluoro, utilizing DABCO as a catalyst;

(e) acylation utilizing an HF-pyridine medium from a prior fluorination step; and (f) acylation of 2-amino-adenosine compounds with subsequent fluorination.

In accordance with the inventive process, the nucleoside guanosine, $C_{10}H_{13}N_5O_5$, i.e., 2-amino-9-β-D-ribofuranosyl- 9H-purine-6(1H)-one, is employed as the starting material in a process for the synthesis of the parent drug fludarabine, $C_{10}H_{12}FN_5O_4$, i.e., 9-β-D-arabinofuranosyl-2-fluoroadenine or 9-β-D-arabinofuranosyl-2-fluoro-9H-purine-6-amine. Fludarabine can then be subjected to phosphorylation to obtain the prodrug fludarabine phosphate, $C_{10}H_{13}FN_5O_7P$.

According to one embodiment, the invention involves a process wherein the guanosine starting material is initially subjected to a hydroxy protection step, whereby the 2'-, 3'-, and 5'-hydroxy groups of the sugar or ribofuranosyl moiety are converted into AcO protecting groups wherein Ac is an acyl group (i.e., Ac is R—CO— wherein R is an organic radical). The hydroxy protection step is followed by halogenation. During the halogenation procedure, the 6-keto group of the base or purine moiety is converted to a halogen, e.g., Cl, Br, or F, preferably F. The 2-amino group is then converted to a 2-fluoro group.

The 6-halogen group is then converted to an amino group to obtain the intermediate 2-fluoro-2',3',5'-tri-O-acyladenosine compound. Next, selective deacylation can be performed, whereby the 2'-AcO protecting group is converted to a hydroxy group. Alternatively, all of the acyl-O-protecting groups can be removed and then the 3',5'-positions subjected to selective protection via a disiloxane bridge. The 2'-hydroxy group is then inverted, thereby converting the ribofuranosyl moiety to an arabinofuranosyl moiety, and the 3'- and 5'-protecting groups (e.g., AcO or disiloxane bridge) and, if present, the 2'-protecting group (AcO), are removed to obtain fludarabine. If desired, the 5'-hydroxy group can then be subjected to selective phosphorylation to obtain fludarabine phosphate. The above reaction procedure, inter alia, is illustrated in Scheme 1 (X=halogen).

Alternatively, conversion of the 6-halo group to a 6-amino group may be performed prior to fluorination of the 2-position, to obtain a 2-amino-2',3',5'-tri-O-acyladenosine intermediate. See compound 3 of Scheme 1 with X being $NH_2$. The 2-amino group is then converted to 2-fluoro to obtain the 2-fluoro-2',3',5'-tri-O-acyladenosine intermediate described above. Furthermore, in this embodiment, a 6-O-sulfonyl group, i.e. —$OSO_2R$, wherein R is an organic radical, preferably 2,4,6-triisopropylphenyl, may be used in place of the 6-halo group. See compound 3 of Scheme 1 with X being —$OSO_2R^4$, and $R^4$ being $CH_3$, $CF_3$, aryl (e.g., phenyl), or aryl substituted by up to three $C_{1-4}$-alkyl and/or $C_{1-4}$-alkoxy groups.

According to another embodiment of the invention, the 6-keto group of guanosine is initially aminated (with or without production of the halo or —$OSO_2R$ intermediate) to form the unprotected intermediate 2,6-diamino-9-β-D-ribofuranosyl-9H-purine, also called 2-aminoadenosine (optionally, the O-acylated compounds can be obtained). See Scheme 2, compound 12. This intermediate compound, optionally, O-acylated, is then subjected to reaction procedures wherein the 2-amino group is converted to fluoro, and, subsequently, with suitable protection of the hydroxy groups, the 2'-hydroxy of the ribofuranosyl sugar moiety is inverted to form an arabinofuranosyl sugar moiety or vice versa, i.e., sugar inversion is performed first, and then the 2-amino group is converted to a 2-fluoro group. See Reaction Scheme 2.

According to another embodiment of the invention, guanosine is initially subjected to sugar inversion, wherein the ribofuranosyl moiety is converted to an arabinofuranosyl moiety to obtain a 9-β-D-arabinofuranosylguanine (also called ara-guanosine) compound which may be unprotected or have acyl or disiloxane protecting groups on the carbohydrate hydroxyl groups. The 6-keto group can then be converted to a 6-amino group and the protecting groups, if present, may be removed to yield 9-β-D-arabinofuranosyl-2,6-diaminopurine (also called 2-amino-araadenosine). The 2-amino group is then converted to a fluoro group, with or without protection of the carbohydrate hydroxyl groups, to obtain fludarabine (F-ara-A).

Conversion of the 6-keto group of ara-guanosine to a 6-amino group may be accomplished directly or, with appropriate protection of the hydroxyl groups, via the 6-halo or 6-$OSO_2R$ derivatives as described above for the analogous ribofuranosyl compound, guanosine. The 2-amino group may also be converted to a 2-fluoro group by the methods described above for the corresponding ribofuranosyl analogs.

Above and below the inventive process is described as employing guanosine as the starting material. However, it should be recognized that it is also possible to use a guanosine derivative as the starting material such as, for example, partially acylated guanosine.

In accordance with the inventive process, protection of 2'-, 3'-, and/or 5'-hydroxy groups by acylation is performed by first preferably suspending or dissolving the unprotected or partially protected nucleoside in a suitable suspension medium. This medium comprises one or more polar aprotic solvents such as N,N-dimethylformamide, N,N-dimethylacetamide, acetonitrile or pyridine. The medium may also contain less polar, aprotic co-solvents such as tetrahydrofuran or 1,4-dioxane or halogenated solvents. The medium preferably further contains an acid scavenger such as an excess of pyridine or one or more equivalents of a tertiary amine such as triethylamine. In most cases, an acyl transfer catalyst such as 4-dimethylaminopyridine can increase the reaction rate and allow the reaction to proceed at a lower temperature. Alternatively, the main solvent can be the carboxylic acid corresponding to the carboxylic anhydride employed as the acylating agent.

The nucleosides exhibit low solubility and complete dissolution is difficult. Therefore, suspensions are often preferred from the aspect of using lower amounts of solvent.

Three or more equivalents of an acylating agent, which may be, for example, an acyl halide such as acetyl chloride or benzoyl chloride, but is preferably a carboxylic anhydride, such as acetic, propionic, isobutyric or benzoic anhydride, is added to the suspension, preferably with stirring. The temperature of the reaction mixture is maintained at about 0° C.–90° C. with exclusion of moisture. Progress of the reaction can be monitored by an appropriate method such as thin layer chromatography (TLC) until the reaction is complete.

Any excess acylating agent is preferably quenched by addition of a hydroxylic solvent (e.g., lower alcohols, such as methanol, or water), and the resulting mixture is preferentially concentrated under vacuum. The acylated product is isolated from the residue by appropriate means, preferably by precipitation from an appropriate solvent or mixture of solvents and recrystallization as needed from the same or from a different solvent or mixture of solvents.

The preferred precipitation solvent is water, or a mixture of water and one or more water-miscible solvents, for example, acetonitrile, ketones such as acetone, or low molecular weight alcohols such as 2-propanol. Suitable recrystallization solvents include these solvents, or mixtures of these solvents with esters such as ethyl acetate, ethers such as tetrahydrofuran (THF) or 1,4-dioxane, and may include lesser amounts of polar aprotic solvents such as N,N-dimethylformamide (DMF), dimethylsulfoxide (DMSO). The resultant precipitate is subsequently collected, preferably by filtration or centrifugation, yielding the desired protected nucleoside.

In an alternative isolation procedure, the residue is partitioned between water and a suitable water-immiscible solvent such as ethyl acetate. The water-immiscible solvent layer can be extracted with a mild aqueous base such as sodium bicarbonate, to remove any residual carboxylic acid derived from the excess acylating agent, and also may be rinsed with either an aqueous acid solution to remove any excess acid scavenger, or an aqueous solution containing cupric ion to remove any residual pyridine. Evaporation of the water-immiscible solvent provides the tri-O-acetylated product. This material is generally of suitable purity for most uses, but may be further purified by common methods such as recrystallization or chromatography as necessary.

Thus, for example, to obtain 2-fluoro-2',3',5'-tri-O-acyladenosine, 2-fluoroadenosine is subjected to acylation, whereby the 2'-, 3'-, and 5'-hydroxy groups of the ribofuranosyl sugar moiety are converted to acyl protected groups, i.e., AcO, wherein Ac is an acyl group having preferably up to twelve carbon atoms, for example, an alkanoyl radical having 1–5 carbon atoms (e.g., acetyl, propionyl, butyryl), benzoyl, benzoyl substituted by one to three $CH_3$, halo, nitro, and/or methoxy groups, naphthoyl, or naphthoyl substituted by a $CH_3$, halo, nitro or methoxy group. Acetyl or benzoyl is preferred. See compound 15 of Reaction Scheme 2.

In addition to the common ingredients listed above, the acylation medium may contain up to 40% by weight of hydrogen fluoride and other components of the diazotization/fluorination reaction mixture. In this case, the acid scavenger present is preferably an aromatic heterocyclic base such as pyridine. Preferably, the amount of hydrogen fluoride does not exceed the amount of acid scavenger, such as pyridine, by more than three fold, on a molar basis. When hydrogen fluoride is present in the medium, the acyl transfer catalyst is preferably omitted from the reaction medium.

The possibility of hydrogen fluoride being present in the acylation reaction medium provides a convenient alternative to the isolation of the unprotected fluoronucleoside from the hydrogen fluoride-pyridine medium employed in a prior conversion of a 2-amino substituent to a 2-fluoro group. In addition, when hydrogen fluoride is present in the reaction mixture, several alternative isolation processes may be employed which take into account the safety concerns when using acidic HF.

For example, the reaction mixture may be combined with an aqueous suspension or solution containing a base and a metal ion which forms an insoluble fluoride salt, such as calcium ion. For example, the reaction mixture may be mixed with an aqueous suspension of calcium carbonate, and the product may be extracted into, or dissolved in a suitable organic solvent and purified as described above.

A preferred alternative isolation procedure is to combine the reaction mixture with an aqueous or alcoholic solution or suspension containing a borate ion species, preferably boric acid, and to collect the resultant precipitate, by filtration or centrifugation. Boric acid is preferred over other common borate species such as sodium tetraborate (borax) or potassium tetraborate because it avoids the risk of forming poorly soluble inorganic salts such as sodium fluoride, potassium fluoroborate, or potassium hydroxytrifluoroborate which could contaminate the acetylated product. Alternatively, or to improve the yield, the aqueous filtrates may be subjected to an extractive isolation process as described above.

To obtain the desired 3',5'-di-O-acyl intermediates, it is preferred to follow a full protection/selective deprotection sequence, rather than a selective acyl protection procedure.

Selective tri-O-acylation of 2-aminoadenosine compounds is reported to fail (Montgomery et al., J. Med. Chem., 1969, 12, 498–504) due to concomitant acylation of the 2-amino group. However, when the acylation is performed under mild acidic conditions, complete O-acylation can be accomplished with only a modest degree of acylation of the purine amino groups. When the acyl group is acetyl, the resulting mixture of products is difficult to separate by recrystallization, but the mixture may be subjected to the diazotization/fluorination process described below and the resulting 2-fluoroadenosine compound can be isolated in moderate yield by crystallization from the crude reaction residue. The undesired N-acyl byproducts, which may or may not become fluorinated, are easily removed by this purification process, because of their high solubility in polar organic solvents and in water, and their low propensity to crystallize.

Acylation may also be employed as a convenient process to recover and recycle partially protected nucleoside byproducts from subsequent steps to increase the overall yield of fludarabine from the synthetic process. For example, acylation can be used to recover mixtures of 2',5'-acyl, 2',3'-acyl and other byproducts from a selective 2'-O-deacylation reaction. In this case, hydrazine or hydroxylamine derivatives such as acyl hydrazides, hydroxyamic acid, hydrazones or oximes may be present in the material to be recycled. If so, it is preferable to add sufficient quantities of acylating agent to ensure complete acylation of these groups and to form the desired tri-O-acyl nucleoside intermediate.

Halogenation in accordance with the inventive process can be performed by a variety of methods. For example, the conversion of a 6-keto group to a 6-chloro or 6-bromo group is preferably performed by a dehydrative halogenation method. This involves dissolving the O-protected starting material in a suitable solvent, preferably acetonitrile. A dehydrating agent and a halogenating agent, preferably a single reagent which performs both of these functions, for example a phosphorylhalide such as phosphorus oxychloride, is added. Preferably, the reaction mixture also contains one or more equivalents of an auxiliary source of the corresponding free halogen ion. Suitable auxiliary halogen sources are tetraalkylammonium halides such as benzyltrimethylammonium chloride. It is preferable that moisture be excluded from the reaction mixture. The reaction mixture is then heated to a temperature of 60°–100° C. for a time period of 5–60 minutes, preferably under reflux. Formation of a solution is not necessary at the beginning of the reaction, but the reaction mixture preferably becomes homogeneous during the heating period. See also Robins et al., Can. J. Chem., 1981, 59, pp. 2601–2607.

The reaction mixture is then concentrated under vacuum and the residue is partitioned between ice/water and a water-immiscible organic solvent such as dichloromethane, or preferably ethyl acetate. The resultant mixture is stirred with ice, and the organic and aqueous layers separated. The organic portion is dried, filtered, and concentrated under vacuum. The desired 6-halo compound, wherein halo is Cl or Br, is purified from the resultant residue by appropriate methods, such as chromatography, or preferably by crystallization with a suitable medium, e.g., 2-propanol.

In order to prepare the corresponding 6-fluoro compound, the 6-chloro or 6-bromo compound can be subjected to halogen exchange. In this procedure, the 6-Cl or 6-Br compound is further treated by dissolving the product of the initial halogenation in a suitable polar, nonprotic solvent such as dimethylformamide (DMF), dimethyl sulfoxide (DMSO) or a ketone solvent, especially acetone, along with a soluble source of fluoride ion to serve as a fluorination agent. Suitable fluorination agents include tetraalkylammonium fluoride salts such as tetrabutylammonium fluoride, or trialkylammonium fluoride salts, or potassium fluoride or cesium fluoride; high surface area potassium fluoride, i.e., spray dried, is preferred.

Conversion of a 6-chloro or 6-bromo compound to a 6-fluoro compound is most efficient when a catalytic amount of an unhindered tertiary amine catalyst, such as trimethylamine, quinuclidine, or preferably 1,8-diazabicyclo[2.2.2] octane (DABCO), is present in the reaction medium. DABCO, which is a solid at room temperature, exhibits several advantages over trimethylamine, which is a gas at room temperature. For example, DABCO provides a higher reaction rate, and is less volatile, so it is less likely to escape from the reaction container during the reaction period and can be handled more conveniently, and measured more accurately than trimethylamine.

After maintaining the resultant solution or suspension at a temperature of about 20°–50° C. for about 6–48 hours, the solution/suspension may be concentrated under vacuum, the residue obtained suspended in a suitable suspension medium such as chloroform or ethyl acetate, and the suspension filtered. The filtrate can be subjected to recrystallization from, for example, 2-propanol, to obtain the corresponding fluoro compound.

See, again, Robins et al., Can. J. Chem., 1981, 59, pp. 2601–2607.

The 6-O-sulfonyl derivative may be prepared by treating the 2',3',5'-tri-O-acyl-guanosine compound with a sulfonic anhydride or sulfonyl chloride in a medium such as pyridine or a halocarbon medium such as dichloromethane along with a tertiary amine such as triethylamine as an acid scavenger.

See the procedure of Bridson et al., J.C.S., Chem. Commun., 1977, pp. 791–792.

Conversion of 6—$OSO_2R^4$ to 6-F should be performed in the presence of DABCO or trimethylamine with a suitable fluorination agent such as potassium fluoride. Conversion of 6—$OSO_2R^4$ to 6-$NH_2$ or 6-$N_3$ can be performed in the presence of an unhindered tertiary amine catalyst using a suitable amination agent such as ammonia. See also the discussion of FIG. 1 below regarding conversion of 6-Cl or 6-Br compounds to 6-azide compounds.

Monohalogenated 6-halo compounds, e.g., the 6-Cl, 6-Br or, preferably, the 6-F compound, which have a 2-amino substituent, as well as non-halogenated 2-aminoadenosine or 2-amino-ara-adenosine compounds, can be subjected to a diazotization/fluorination process to obtain a 2,6-dihalo compound (e.g., chlorofluoro or difluoro) or 2-F-6-amino compounds, respectively.

For example, a 6-fluoro-2-amino compound can be subjected to further fluorination using a diazotization agent, for example, an alkyl nitrite, preferably tert.-butylnitrite, or an inorganic nitrite, such as sodium nitrite, or more preferably potassium nitrite, and a fluorination agent, e.g., fluoboric acid, or preferably HF-pyridine, at a temperature of −30° C.–+30° C., preferably −15° C. to 0° C.

The preferred medium is a mixture of hydrogen fluoride and pyridine containing 50–70 wt.%, or more preferably 55–60 wt.%, hydrogen fluoride. The medium may be anhydrous. But, if an inorganic nitrate, such as potassium nitrite, is employed, it is preferably added to the reaction mixture as a concentrated aqueous solution. The resultant mixture is maintained within the above-mentioned temperature range for about 10–120 minutes.

The HF-pyridine reaction and isolation of 2-fluoro compounds, without acyl protection, from the resultant reaction medium is further described in related copending application Ser. No.07/981,333.

The desired product is then isolated or subjected to a subsequent reaction in the same medium. For example, if hydrogen fluoride-pyridine was employed as the fluorination medium and the product has one or more acyl protection groups which impart organic solubility, the reaction mixture may be partitioned between water in an organic solvent, such as dichloromethane or preferably ethyl acetate. The aqueous and organic layers are allowed to separate, and may be extracted with water, then with a mild aqueous base such as sodium or potassium bicarbonate, to remove excess hydrogen fluoride, and optionally, with dilute aqueous mineral acids, or an aqueous cupric ion solution to remove residual pyridine. The organic extract is dried, filtered, and concentrated under vacuum. If the mineral acid or cupric ion washes are not employed, the resultant residue may be resuspended or redissolved in a suitable high boiling solvent, such as toluene, and concentrated in a vacuum to remove any residual pyridine.

In an alternative isolation procedure which is preferred when hydrogen fluoride-pyridine is used as the fluorination agent and all hydroxyl groups are protected by acyl groups, the reaction mixture is combined with an aqueous solution or suspension of a borate species, such as borax or preferably boric acid. The resultant precipitate is collected by filtration or centrifugation, and may be further purified as described above. Alternatively, or to increase yields, the product of the reaction may be extracted into a water-immiscible solvent such as ethyl acetate, and purified according to the general extraction procedure described above. The suspension or solution obtained by combining the reaction mixture with the borate mixture, may optionally be neutralized as desired, by addition of a mild base, or an aqueous buffer solution. If pyridine is present in the fluorination medium, the preferred base is pyridine, and additional pyridine may be added as needed.

The use of borate in the above work-up procedure converts the excess hydrogen fluoride from the fluorination medium into fluoroborate species such as fluoborate ion ($BF_4^-$) or hydroxytrifluoroborate ion ($BF_3(OH)^-$). This procedure has several advantages over the previously described isolation procedures. First, the concentration of the corrosive and volatile hydrogen fluoride is decreased substantially, which makes this procedure more safe and convenient. Second, the amount of base needed to neutralize the reaction mixture and thus the amount of inorganic water generated is substantially reduced. Both of these advantages facilitate scale-up.

The resultant 2,6-dihalo or 2-fluoro-6-amino compound is obtained as an oily residue, or as a solid. The residue can then be used in subsequent steps (e.g., amination of the 6-position, conversion of the sugar moiety) without further purification. If, however, purification is desired, the product can be purified by appropriate means such as chromatography, or by crystallization with a suitable solvent, for example, 2-propanol.

Diazotization/fluorination of unprotected 2,6-diaminopurine nucleosides in a medium such as HF-pyridine requires special methods for isolation of the resulting fluoroadenine compounds. Procedures for the isolation of fluoroadenine nucleosides are disclosed in related copending application Ser. No. 07/981,333. In an alternative process, isolation of the unprotected fluoronucleoside may be advantageously avoided, by converting it to the corresponding tri-O-acylated compound prior to work-up.

For example, after 2-aminoadenosine has been fluorinated in a medium of 50–70% HF-pyridine, an acylating agent, preferably a carboxylic anhydride such as propionic anhydride or most preferably acetic anhydride, may be added to the reaction medium. An acyl transfer catalyst such as 4-dimethylaminopyridine (DMAP) may also be added. In a medium such as HF-pyridine, the carboxylic anhydride may also react with HF to form an acyl fluoride, which is a poor acylating agent. Therefore, to suppress this competing reaction to a manageable level, it is preferred that the proportion of HF in the medium be decreased prior to addition of the anhydride. A convenient and preferred means to decrease the proportion of HF is to dilute the reaction with anhydrous pyridine so that the molar ratio of HF:pyridine is between 3:1 and 1:1. At higher ratios the formation of acylfluoride is rapid, so a many fold excess of the acylating agent is required, and degradation of the product may occur prior to completion of the acylation reaction. To decrease this ratio below 1:1 requires large amounts of pyridine. In either case, the additional pyridine or acylating agent can interfere with the preferred isolation procedure.

For the acylation process, the preferred molar ratio of HF:pyridine is about 2:1, or about 34% HF on a w/w basis. Under these conditions, the highest yields of tri-O-acylated compound is obtained when about 5–10 molar equivalents (relative to the amount of 2-aminoadenosine) are used. Somewhat greater amounts may be required if water is present in the fluorination reaction medium, for example when an alkali metal nitrate has been added as an aqueous solution.

The acylation reaction is then allowed to proceed for 4–48 hours at 15°–40° C., or preferably overnight at ambient temperature. When acylation is complete, as determined by an appropriate method, such as HPLC or TLC, the tri-O-acylated compound may be isolated by one of the procedures described above, most preferably via the borate procedure.

Thus, after the diazotization/fluorination and acylation reactions are complete, the reaction is preferably mixed with an aqueous solution or suspension of boric acid and the resulting precipitate is collected by filtration or centrifugation and washed with water and/or an alcoholic solvent to remove the residual water-soluble reaction components. The collected solid, crude 2-fluoro2',3',5'-tri-O-acyl compound, may then be purified further as described under the discussion of the acylation process. If no precipitate is collected, or to increase the yield, the filtrates may be extracted with an organic solvent to obtain additional material. This will typically require further purification by chromatography or recrystallization, prior to use in subsequent reactions.

The convenience of this acylation process and of the borate isolation process makes this sequence a convenient alternative to the isolation of the unprotected 2-fluoroadenine nucleoside. This process is particularly preferred if the selective deprotection process, to produce a 3',5'-di-O-acyl intermediate, is employed for the subsequent conversion of the ribofuranosyl moiety to an arabinofuranosyl moiety. This process also affords a convenient opportunity to purify the intermediate compound shortly after the fluorination step.

The most significant advantage of this process is demonstrated by the preferred example, wherein the product is 2-fluoro-2',3',5'-tri-O-acetyladenosine. When the borate work-up procedure is employed, the desired product is the only significant component of the reaction mixture that is not highly soluble in the aqueous mixture obtained after the reaction is quenched with boric acid. Thus, the product can be isolated in good yield and high purity by filtration or centrifugation, and little or no additional organic solvents are required. Furthermore, the low solubility of this compound in most common organic solvents at ambient temperature makes this a convenient compound to purify further and with high recovery, by recrystallization. The low solubility of this compound obviates the need for an extractive isolation process.

The above-described dehydrative halogenation procedure can be used to provide halogen atoms, Cl or Br, at the 6-position. A F atom can then be inserted at the 6-position by halogen exchange. Finally, diazotization/fluorination can be used to convert 6-Cl-2-$NH_2$, 6-Br-2-$NH_2$, or 6-F-2-$NH_2$ compounds to dihalogenated compounds, i.e., 6-Cl-2-F, 6-Br-2-F, and 6-F-2F compounds, respectively. Furthermore, the diazotization/fluorination procedure can also be used to introduce a F atom at the 2-position of the adenine moiety of adenosine nucleosides from 2-amino-adenosine nucleosides.

These general methods of halogenation are independent of the configuration of the chiral centers of the furanosyl carbohydrate moiety of the nucleoside. Thus, these methods may be applied to nucleosides which possess either the ribofuranosyl or arabinofuranosyl moiety. Typically, the hydroxy groups of the furanosyl moiety are protected during halogenation. However, in the case of 2-amino-adenosine or 2-amino-ara-adenosine, fluorination of the 2-position can be performed without protecting the hydroxy groups of the sugar moiety. See Reaction Scheme 2, compound 12 to compound 7, and Reaction Scheme 2, compound 17 to compound 10. Following fluorination of the 2-position, acyl protection of the hydroxy groups can be introduced. See Scheme 2, compound 7 to compound 15.

In a preferred sequence, a 2',3',5'-tri-O-acylated guanosine nucleoside (compound 2) is, for example, subjected to a first halogenation step (i.e., dehydrative halogenation), whereby the 6-keto group is converted to Cl (compound 3, X=Cl) to obtain 2-amino-6-chloro-9-β-D-(2',3',5'-tri-O-acylribofuranosyl)-9H-purine. A fluorination step (i.e., halogen exchange) can then be carried out to obtain the corresponding 6-fluoro compound (compound 3, X=F). A further fluorination step can then be performed to obtain the difluoro compound, 2,6-difluoro-9-β-D-(2',3',5'-O-acylribofuranosyl)-9H-purine (compound 4, X=F). See also Reaction Scheme 5.

Amination of a dihalo compound in the inventive synthesis process is conducted, for example, by initially dissolving the dihalo compound, most preferably a difluoro compound, in a suitable anhydrous nonprotic solvent, which is preferably an ether such as tetrahydrofuran (THF), 1,4-dioxane, or 1,2-dimethoxyethane. Protic solvents such as alcohols should be avoided, unless it is desirable to remove the O-acyl protecting groups concomitantly with the amination process. See Montgomery et al., J. Org. Chem., 1968, 33, p. 432.

This amination is preferably accomplished by bubbling in anhydrous ammonia, at a temperature of about 10°–30° C. until the dihalo compound is consumed, for example, as determined by a suitable analytical method such as TLC or HPLC. The resultant mixture is concentrated under vacuum to obtain a crude residue which may be further purified by various methods such as chromatography, partition between water and an organic solvent such as ethyl acetate or a halocarbon solvent, or dissolution of the product in an organic solvent such as ethyl acetate or a halocarbon solvent and removal of the inorganic precipitate by filtration or extraction into an aqueous solution. Final purification is preferably accomplished by recrystallization from a suitable solvent or combination of solvents, which may include water in addition to a large variety of organic solvents such as simple amides, esters, ethers, alcohols, ethers, halocarbons or hydrocarbons, depending on the identity of the hydroxyl protecting groups.

See also Robins et al., Can. J. Chem., 1981, 59, pp. 2608–2611.

The 2,6-dihalo intermediates, as shown in, for example, the reaction scheme, are preferably obtained without purification of the crude product and directly subjected to amination, wherein the 6-halo (preferably 6-F) group is converted to a 6-amino group obtain a 2-halo-2',3',5'-tri-O-acylated-protected-adenosine. The 6-chloro-2-fluoro and 6-bromo-2-fluoro compounds are not preferred substrates in the amination reaction, because amination leads to a mixture of 2-fluoroadenosine and 2-amino-6-chloropurinenucleoside or 2-amino-6-bromopurinenucleoside compounds. This results in a reduced yield of the desired fluoroadenosine compound and complicates its isolation.

Amination by this process may also be employed as a means to increase the yield of the diazotization/fluorination process when it is applied to the fluorination of O-acyl protected 2-aminoadenosine compounds as described above. Due to the less than complete selectivity of the diazotization/fluorination process in this case, and particularly when an excess of the diazotization agent is used, significant amounts of the corresponding 2,6-difluoro compound may be formed. The difluoro compound may be converted to the desired fluoroadenosine compound by this amination process.

The amination may be performed either on the crude mixture of difluoronucleoside and fluoroadenosine compounds. Alternatively, these compounds may be separated, for example, by crystallization of the fluoroadenosine compound, and then the difluoro compound, which is recovered from the mother liquors of this crystallization, can be aminated. This process is particularly useful when the fluorination is performed on the crude mixture of products obtained from the acylation of aminoadenosine or amino-ara-adenosine, because the amount of diazotization agent required may be difficult to estimate due to variability in the level of N-acylation. See compound 12 to compound 14 to compound 15, of Reaction Scheme 2.

Amination of 2-amino-6-halo nucleoside compounds, is preferably accomplished via a two-step process, wherein the halo group is first displaced by an azido group, with trimethyl amine as catalyst. The azido group is subsequently reduced to an amino group (as described by Robins et al., Can. J. Chem., 1981, 59, 2601) to form the 2-aminoadenosine compound. In a preferred process, DABCO is employed as the catalyst for the halide displacement process, as described above in the case of halide exchange reactions.

Direct amination of guanosine may be accomplished by the process described by Vorbrüggen et al., Liebigs Ann. Chem., 1976, 745–761, wherein, the nucleoside is first subjected to persilylation, and subsequently heated with an ammonia compound. In this process, the silyl groups are preferably trimethylsilyl, and these groups are removed in the isolation process to form 2-aminoadenosine. In a similar manner, amination of ara-guanosine produces 9-β-D-arabinofuranosyl-2,6-diaminopurine (2-amino-ara-adenosine).

Complete removal of the 2'-, 3'-, and 5'-O-acyl protecting groups, can be performed in a variety of ways. Removal of O-acyl protecting groups from 2-fluoroadenine nucleosides have been described by, for example, Montgomery et al. (J. Org. Chem., 1968, 33, 432), who used ethanolic ammonia to produce 2-fluoroadenosine. Secrist et al., J. Med., Chem., 1988, 31, pp. 404–410, used lithium hydroxide to produce 2,2'-difluoro-ara-2'-deoxyadenosine. These are general methods which can be applied to the deprotection of O-acyl protected nucleosides, including 2-fluoroadenosine, with various furanosyl carbohydrate moieties.

In addition to lithium hydroxide, other hydroxides, such as sodium or potassium hydroxide may also be employed for the hydrolytic cleavage of O-acyl groups. However, when these other hydroxides are used to remove O-acyl groups from 2-fluoroadenine nucleosides, special care should be taken to control the reaction time and temperature, and to avoid the use of excessive hydroxide reagent.

Each of these methods have the potential for production of contaminants wherein the 2-fluoro substituent has been displaced by the deprotection agent to form basic 2-amino, 2-hydroxy, or 2-alkoxy adenosine compounds. In accordance with a preferred aspect of the invention, a method is employed for removing these impurities, which involves passing an aqueous alcohol solution of the crude product through a column of sulfonic acid ion exchange resin.

To accomplish inversion of the 2'-hydroxyl group, it is necessary to differentiate the 2'-hydroxyl group from the 3'- and 5'-hydroxyl groups. One means to accomplish this is through the use of bulky disiloxane type protecting groups, which first react selectively with the less hindered primary 5'-hydroxyl group, then cyclizes to form a bridge between the 5'-and 3'-hydroxyl groups. Examples of disiloxane protecting groups are 1,1,3,3-tetra-t-butoxydisiloxane-1,3-diylidine (TBDS), described by Markiewicz et al., Tetrahedron Lett., 29, 1561, 1988, 1,1,3,3-tetraisopropyldisiloxane-1,3-diylidine (TIPDS), employed by Secrist et al., J. Med. Chem., 1988, 31, pp. 405–410, and 1,1,3,3-tetraphenyldisiloxane-1,3-diylidine (TPDS) for protection of 2-fluoroadenosine.

A preferred alternative means to prepare a 3',5'-di-O-protected nucleoside is to selectively remove the 2'-O-acyl group from a fully hydroxyl acylated nucleoside derivative. Use of hydrazine in 4:1 pyridine:acetic acid, or hydroxylammonium acetate in pyridine or alcoholic solvents, to accomplish this type of selective deprotection is described by Ishido et al., J. Chem. Soc. P1, 1979, 2088 and idem. 1980, 563. As reported therein, this method leads to formation of a mixture of products, which have had one or both of the 2-' or 3'-O-acyl protecting groups removed. In addition, these isomeric mono-deprotected products are known to interconvert (i.e., to equilibrate) under various conditions, such as those of the reaction, and under typical purification methods. Therefore, the success of this method rests in the ability to selectively isolate the desired isomer, rather than in the inherent selectivity for removal of one or the other acyl groups.

As a result of the equilibration, it is not possible to predict, a priori, which isomer will be isolated in a given example. In some cases, subtle changes in the isolation process can lead to the exclusive isolation of the undesired isomer, or a mixture of isomers, so the reaction can be capricious.

However, this capriciousness problem is not exhibited by a preferred aspect of the inventive process described below wherein selective deacylation is performed on 2-fluoro-2', 3',5'-tri-O-acyladenosine The ease with which the desired isomer can be isolated is highly dependent on the identity of the heterocyclic base (e.g., purine or pyrimidine, etc.) and on its substituents, and on the identity of the O-acyl protecting groups because these determine the relative solubilities of the various components of the crude reaction mixture, and thus the likelihood that the desired product can be isolated, preferably, by crystallization from the crude mixture.

When the substrate is a 2',3',5'-tri-O-acyl-2-fluoroadenosine compound, the preferred acyl group is acetyl, because this allows the desired isomer to be isolated easily, in high purity by crystallization of the crude reaction mixture.

The above papers by Ishido et al. give several examples of suitable combinations of protecting groups for guanosine which make it possible to isolate the desired 3',5'-di-O-acyl intermediate, and described a method for using these to make ara-guanosine. Some of the selective deacylation procedures described by Ishido et al. produce a predominant portion of the 2',5'-di-O-acyl compounds Furthermore, these authors do not describe the selective deprotection of halogenated nucleosides.

As mentioned above, the disadvantages of Ishido et al. are not exhibited when the 2-fluoro-tri-O-acetyl compound is subjected to selective deprotection. For example, referring to Reaction Scheme 1, compound 4 (X is F and R is acetyl), is subjected to selective deacylation, wherein, e.g., the acetyl-O-group in the 2'-position of the ribofuranosyl moiety is converted to a hydroxy group to obtain 2-fluoro-9-β-D-(3',5'-di-O-acylribofuranosyl) -9H-adenine. See compound 5. This product can be easily isolated and obtained in high purity.

To perform the selective deacylation, the starting material and a deacylation agent are combined as a solution or a dispersion in a suitable medium and the reaction is conducted at a temperature of about 15°–80° C. for about 1–50 hours. The appropriate reaction time can be determined by monitoring the reaction by a suitable method such as thin layer chromatography (TLC) or HPLC, and the excess reagent is quenched when the amounts of the triacyl starting material and the over-reaction product, i.e., the 5'-mono-O-acetyl compound, are comparable. The reaction medium may contain one or more solvents such as pyridine or an alcoholic solvent having up to four carbon atoms such as methanol or 2-methoxyethanol, and may contain up to 25% by volume of a carboxylic acid having up to 8 carbon atoms, and up to 20% by volume of water.

Suitable deacylation agents include hydroxylamine, or hydrazine and soluble carboxylate salts thereof such as hydroxylammonium acetate. The deacylation/hydroxylation agents may be prepared in a separate step by known means from commercially available materials, or preferably may be generated, in the reaction medium, by combining appropriate commercially available salts. For example, a suitable solution of hydroxylammonium acetate in pyridine may be generated by mixing a suspension of hydroxylamine hydrochloride and sodium or potassium acetate in pyridine.

The resultant product is then isolated and subjected to further purification as appropriate. The preferred isolation method is to quench any residual deacylation agent by adding an excess of a ketone solvent such as acetone and to concentrate the reaction mixture, preferably under vacuum. The resultant crude residue is then suspended in an appropriate crystallization medium and any solid precipitate is collected by filtration or centrifugation. The preferred crystallization medium is water, or an alcoholic solvent in which the reaction byproducts but not desired product are soluble. The crystallized product may be further purified as needed, by recrystallization or preferably by slurrying with a suitable solvent, or mixture of solvents such as those suitable for recrystallization of the tri-O-acetylated intermediates as described above.

For example, the preferred product of this reaction, 3',5'-di-O-acetyl-2-fluoroadenosine, may be isolated by suspending the crude reaction residue in water and collecting the resultant precipitate. The precipitate, which typically contains nucleoside compounds, is then slurried, with heating, in a solvent or a mixture of solvents such as ethyl acetate or acetonitrile and acetone. Upon cooling the mixture, the resultant precipitate is again collected, washed and dried.

Alternatively, as shown in Reaction Scheme 1, the 2-fluoro-6-halo-2',3',5'-tri-O-acyl compound (compound 4; X=halo) can be converted directly into the unprotected compound, 2-fluoro-adenosine, via complete deacylation and amination, i.e., 2-fluoro-adenosine (see compound 7). The deacylated compound can then be subjected to selective protection of the 3',5'-positions of the ribofuranosyl moiety via a disiloxane bridge (see compound 5; both $R^1$ groups together=$O((Z)_2Si)_2$). This procedure can be used if it is desired to have the 3',5'-positions protected with a bridge during the sugar conversion rather than 3'- and 5'-acyl groups.

Conversion of the sugar moiety from a ribofuranosyl moiety, such as exhibited by guanosine to an arabinofuranosyl moiety, such as possessed by fludarabine involves inverting the stereochemical orientation of the 2'-stereocenter of the ribofuranosyl moiety. Conversion is preferably carried out using a partially protected compound as the starting material wherein the 3'- and 5'-positions are protected by, for example, O-acyl-groups or a bridging group such as tetraisopropylsiloxane or tetra-tert.-butoxy disiloxane. The sugar conversion, as illustrated in the reaction schemes, proceeds by way of an oxo intermediate or a sulfonyloxy intermediate.

Conversion for non-halogenated nucleoside compounds can proceed via the oxo intermediate as described by Sakairi et al., Nucleosides, & Nucleotides, 1983, 2, 221–229, who employed O-acyl protecting groups; Samano et al., J. Org. Chem., 1990, 55, 5186–5188; and Hansske et al., Tetrahedron, 1984, 40, 125–135, who employed silyl and other O-protection groups. First, the selectively protected substrate is treated with a suitable oxidizing agent to convert the 2'-hydroxyl group to a keto group. Second, the keto intermediate is treated with a suitable reducing agent to preferentially reduce the keto intermediate in a stereoselective manner to produce the desired arabinofuranosyl compound as the major reduction product. The oxidation and reduction steps may be performed in separate reaction steps, but are preferentially performed without isolation of the intermediate keto intermediate.

Examples of suitable oxidizing agents are described by Samano et al. (see above). The typical reagents are (1) certain chromium (VI) reagents; (2) Swern-Moffatt-Pfitzner (SMP) type oxidizing agents, prepared by combining dimethylsulfoxide (DMSO) and a dehydrating agent; and (3) periodinane reagents such as the Dess-Martin periodinane reagent (1,1,1-tris(acetyloxy)-1,1-dihydro-1,2-benziodoxol-3 (1H)-one). For example, a suitable method using a chromium (VI) reagent, employs a mixture of $CrO_3$, pyridine, and acetic anhydride in a halogenated solvent such as dichloromethane.

Suitable dehydrating agents for the SMP type of reagent system, are inorganic or carboxylic anhydrides or acid chlorides, such as acetic or trifluoroacetic anhydride, oxalyl chloride, phosgene (or its oligomers), sulfurtrioxide-pyridine, phosphorous pentoxide, or carbodiimides, such as 1,3-dicyclohexylcarbodiimide. When these reagents are employed, DMSO may serve as the reaction medium, which may also contain a halogenated solvent such as dichloromethane if the substrate is sufficiently soluble in this solvent, and a mild base such as pyridine or triethylamine.

The preferred reaction temperature and reaction time are dependent on the reactivity of the dehydrating agent. With the more powerful dehydrating agents such as oxalychloride, the preferred temperature is about –90° C.—50° C. For more mild agents such as acetic acid, temperatures of 15°–30° C. are preferred. In general, reaction times of 6–50 hours may be required.

If the periodinane reagent is used, the preferred solvent is a halocarbon. Therefore, this type of reagent is only preferred when the substrate is soluble in the halocarbon solvent, such as when it is protected by means of a disiloxane type of protecting group.

Conversion of the oxo intermediate to obtain an arabinofuranosyl compound is accomplished by reduction with a mild hydride reducing agent. The medium for the reduction process may include the components of the oxidation reaction if the SMP conditions are employed, although halogenated solvents are not preferred. The medium may also contain a protic solvent such as ethanol or a carboxylic acid, or ether solvents such as tetrahydrofuran. The preferred reducing agent is sodium borohydride, or other species, such as sodium triacetoxyborohydride, which may be formed from sodium borohydride under the reaction conditions.

The oxidation/reduction method for converting a ribofuranosyl moiety into an arabinofuranosyl moiety have a number of drawbacks which detract from their commercial viability as processes for the production of fludarabine, or fludarabine phosphate. Many of these methods depend on the use of halogenated solvents as reaction media, which involve environmental concerns. The chromium reagents involve additional environmental concerns. Periodinane reagents are available in only limited quantities, due to their instability, and reports of their potential for detonation. The SMP oxidation methods, are known to lead to the formation of various types of byproducts which decrease yields, and complicate purification of the arabinofuranosyl products. These byproducts may be derived from either the substrate (acylation or methylthiomethylation of the 2'-hydroxyl group may occur, rather than oxidation), or the oxo product, which is vulnerable to other reactions under the SMP conditions, particularly if O-acyl groups are used to protect the other hydroxyl groups.

The oxidation reactions can be difficult to monitor due to the known instability of the oxo intermediates. In addition, the reduction step may not be stereospecific. Thus, reduction may produce some ribofuranosyl byproduct (i.e., regeneration of the precursor of the oxo intermediate), in addition to the desired arabinofuranosyl product. This necessitates the separation of isomeric products which can be problematic, and may require chromatographic separation, which would be economically undesirable.

Therefore, when, for example, the purine moiety is 2-fluoroadenine, the sulfonyloxy inversion method described below is preferred, rather than the oxidation/reduction process. However, when the substrate is a protected guanosine or 2-aminoadenosine compound, the oxidation/reduction method (as described above) is preferred over the sulfonyloxy inversion, due to the reactivity of these purine groups with the sulfonylating agent, and other complications.

Preparation of sulfonyloxy intermediates may be accomplished according to the methods of Secrist et al., J. Med Chem., 1988, 31, 405–410; or Jiang et al., Nucleosides & Nucleotides, 1988, 7, 271–294. The 2'-hydroxy -3',5'-O-protected-ribofuranosyl compound is suspended or dissolved in a halogenated solvent or pyridine, treated with triethylamine and 4-dimethylaminopyridine and also treated with a sulfonylating agent such as trifluoromethanesulfonyl chloride or trifluoromethanesulfonic anhydride. In accordance with the invention, the 2'-hydroxy is converted to a sulfonyloxy group of the formula —$OSO_2R^2$ wherein $R^2$ is preferably a strongly electron-withdrawing group such as perfluoroalkyl or perfluoroaryl, e.g., $C_{1-4}$-perfluoroalkyl or perfluorophenyl. Preferably, $R^2$ is $CF_3$.

In a preferred procedure, the reaction medium is pyridine and no tertiary amine or 4-dimethylaminopyridine are added, because these interfere with isolation of the reaction product and also may promote undesired side reactions. Preferably, the sulfonylating agent is a sulfonic anhydride, rather than a sulfonyl chloride, because sulfonylation can be conducted under more mild conditions (i.e., more rapidly, and/or at lower temperatures). This minimizes the formation of undesired side-products. For example, when O-acyl protecting groups are employed, if the sulfonylation is excessively slow, isomerization of the 3',5'-diprotected intermediate might occur, which could lead to the formation of the undesired 3'-O-sulfonyl compound. Sulfonic anhydride precludes substitution of the sulfonyloxy product by chloride. The most preferred sulfonylating agent is trifluoromethanesulfonic anhydride.

The reactants are preferably combined as a suspension at 10°–30° C., and preferably stirred at this temperature for 1–24 hours or until the reaction is complete, as determined by a suitable method such as TLC or HPLC. Under these conditions, the product may then be isolated by simply diluting the reaction mixture with water or by concentrating the reaction mixture under vacuum and diluting the mixture with water. The precipitate which forms can be collected by filtration or centrifugation. This is the preferred isolation method. However, if further purification or increased yield is desired, an extractive workup as described for the acylation process above may be employed. If additional purification is required, the crude product may be purified by chromatographic methods or by recrystallization from a suitable solvent.

Conversion of the 2'-O-sulfonylribofuranosyl moiety into the desired arabinofuranosyl moiety, is accomplished by nucleophilic displacement of the sulfonyloxy group with a suitable oxygen-centered nucleophile such as a nitrite, or preferably a carboxylate species. Suitable carboxylate species include an alkyl or aryl carboxylate ion, for example, acetate, propionate, benzoate, or substituted benzoate such as 4-nitrobenzoate.

The process is accomplished by combining the sulfonyl compound and 1–10 molar equivalents of an oxygen nucleophile in a suitable polar, aprotic solvent such as ethyl acetate, DMSO, or DMF. The reaction medium may also contain up to 25% by volume of one or more protic species, such as water, and up to 10% by volume of the carboxylic acid corresponding to the carboxylate species. These protic species may be added if necessary, to achieve a homogeneous reaction mixture, when alkali metal salts are employed, in solvents such as DMF or DMSO. Excessive amounts of protic species will tend to inhibit the intended reaction, and may promote competitive elimination reactions. Crown ether phase-transfer-catalysts, for example, 18-crown-6 may also be used to help solubilize the sodium or potassium salts, if desired. Excessive amounts of water may lead to heterogeneity, if a water-immiscible solvent such as ethyl acetate is the major component of the reaction medium, so water should be kept to a minimum in this case.

The nucleophile may be introduced to the reaction mixture in the form of a suitable alkali metal salt, wherein the alkali metal is sodium, potassium, or cesium, or as a trialkyl or tetraalkyl ammonium salt, or as the salt of other highly organic soluble cations commonly employed as phase transfer agents, such as tetraalkylphosphonium salts, for example, tetraphenylphosphonium. These salts may or may not be solvated, e.g., they may contain water as in sodium acetate trihydrate, or in the case of carboxylate salts may contain the corresponding carboxylic acid (up to 50% by weight). The ammonium ion of suitable alkyl ammonium salts preferably contain 6–20 carbon atoms, for example, triethylammonium, diisopropylethylammonium, benzyldiethylammonium, benzyltrimethylammonium, or tetrabutylammonium.

Alternatively, the salt of a carboxylic acid may be generated in situ, by combining a suitable base, for example, a trialkylamine, and one or more molar equivalents of the desired carboxylic acid. In situ generation of the trialkylammonium salt allows a convenient method to introduce carboxylate species, especially those which are only commercially available in the corresponding carboxylic acid form.

Under some conditions, the reaction will be complete in less than 4 hours at ambient temperature. Under other conditions, it may be necessary to heat the mixture for as long as 48 hours at a temperature as high as 100° C., but preferably not higher than the normal boiling point of the reaction mixture.

In a preferred method, the sulfonyl compound, e.g., 3',5'-di-O-acetyl-2-fluoro-2'-O-trifluoromethanesulfonyladenosine, an excess of a tertiary amine, preferably 1.5–4 equivalents of triethylamine or diisopropylethylamine, and a similar, or greater excess of a carboxylic acid, preferably 1.5–5 equivalents of acetic acid, propionic acid or benzoic acid, are combined in ethyl acetate and heated to reflux to obtain a homogeneous mixture. The reaction is heated overnight, then optionally concentrated under vacuum. The resulting residue is suspended in water, and the resulting precipitate is collected by filtration, or centrifugation, and washed with water and/or an alcohol solvent such as methanol. This is the preferred isolation method; however, if further purification or increased yield is desired, an extractive workup as described for the acylation process above may be employed. If additional purification is required, the crude product may be purified by chromatographic methods, or by recrystallization from a suitable solvent.

In an alternative preferred process, the sulfonyl compound, e g , 3',5'-di-O-acetyl-2-fluoro-2'-O-trifluoromethanesulfonyladenosine, and an excess of an alkali metal carboxylate salt, preferably 1.2–4 equivalents of, for example, potassium acetate or sodium benzoate, are dissolved in a mixture of DMF or DMSO and water (about 10:1) and heated at 40°–60° C. overnight. The mixture is then diluted with 2–10 volumes of water and the precipitate is collected and further purified as described above to afford, for example, 2-fluoro-9-β-D-(2',3',5'-tri-O-acetylarabinofuranosyl)adenine, or 9-β-D-(2'-benzoyl-3',5'-di-O-acetylarabinofuranosyl)-2-fluoroadenine.

In another preferred process, the sulfonyl compound, e.g., 3',5'-di-O-acetyl-2-fluoro-2'-O-trifluoromethanesulfonyladenosine and an excess of an alkali metal carboxylate salt, preferably 1.2–3 equivalents of a cesium carboxylate salt such as cesium propionate-propionic acid complex are dissolved in a polar aprotic solvent such as DMF or DMSO, and stirred at ambient temperature for 4–24 hours The product, e g , 9-β-D-(3',5'-di-O-acetyl-2'-O-propionylarabinofuranosyl)-2-fluoroadenine, is isolated by diluting the mixture with water. The resulting precipitate is collected and further purified as described above.

When only O-acyl protecting groups are present, complete deacylation can be employed, as described above, to yield fludarabine from 2',3',5'-tri-O-acyl-2-fluoro-araadenosine. Desilylation can be performed by various methods, and most involve the use of fluoride ion as the deprotection agent. Desilylation of nucleoside compounds has been reviewed by Zhang et al., *Tetrahedron Lett.*, 1992, 33, 1177–1780. One of the most powerful desilylation agents is tetrabutylammonium fluoride, which is typically used in a solvent such as tetrahydrofuran (THF). Other fluoride reagents such as triethylamine-hydrogen fluoride complexes or hydrogen fluoride-pyridine complexes are also suitable. As noted by Zhang et al., ammonium fluoride is an inexpensive and convenient reagent for the removal of disiloxane protecting groups from nucleoside compounds, and methanol is used as the reaction medium.

If both O-silyl and O-acyl protecting groups are present, both types of protecting groups are preferably removed in a single step, or in consecutive steps, without purification of the partially deprotected intermediate. If the deprotection is performed in two separate steps, deacylation may precede desilylation, or vice versa. However, if desilylation is performed first and isolation of the desilylated intermediate is desired, $R^3$ should be selected to facilitate isolation of the intermediate by crystallization. In such a case, $R^3$ is preferably aroyl or substituted aroyl.

Fludarabine phosphate can be obtained by phosphorylation of fludarabine in accordance with conventional procedures. See, e.g., U.S. Pat. No. 4,357,324.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
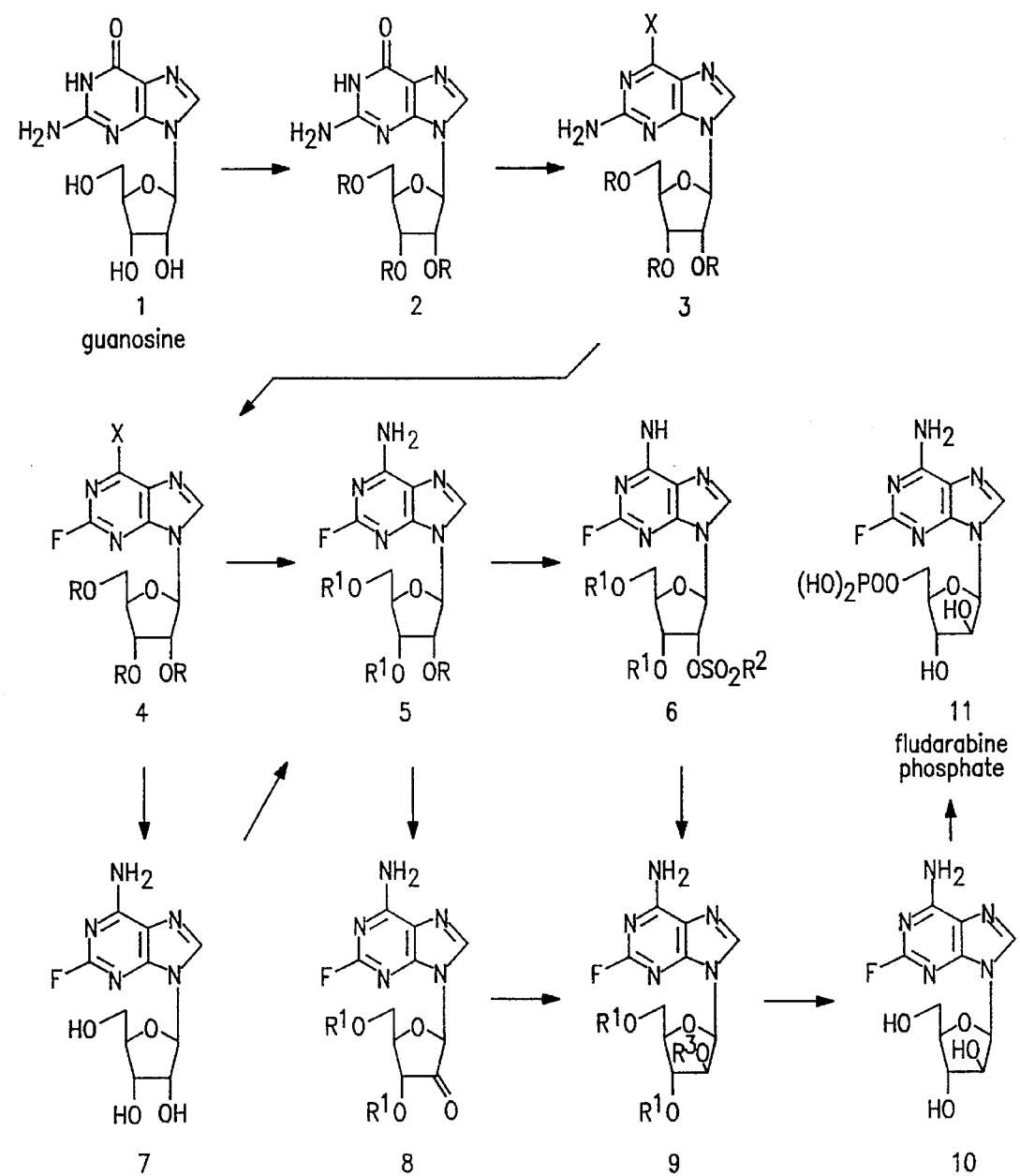
FIG. 1 (Reaction Scheme 1) illustrates a general reaction procedure in accordance with the present invention.
Figure 2:
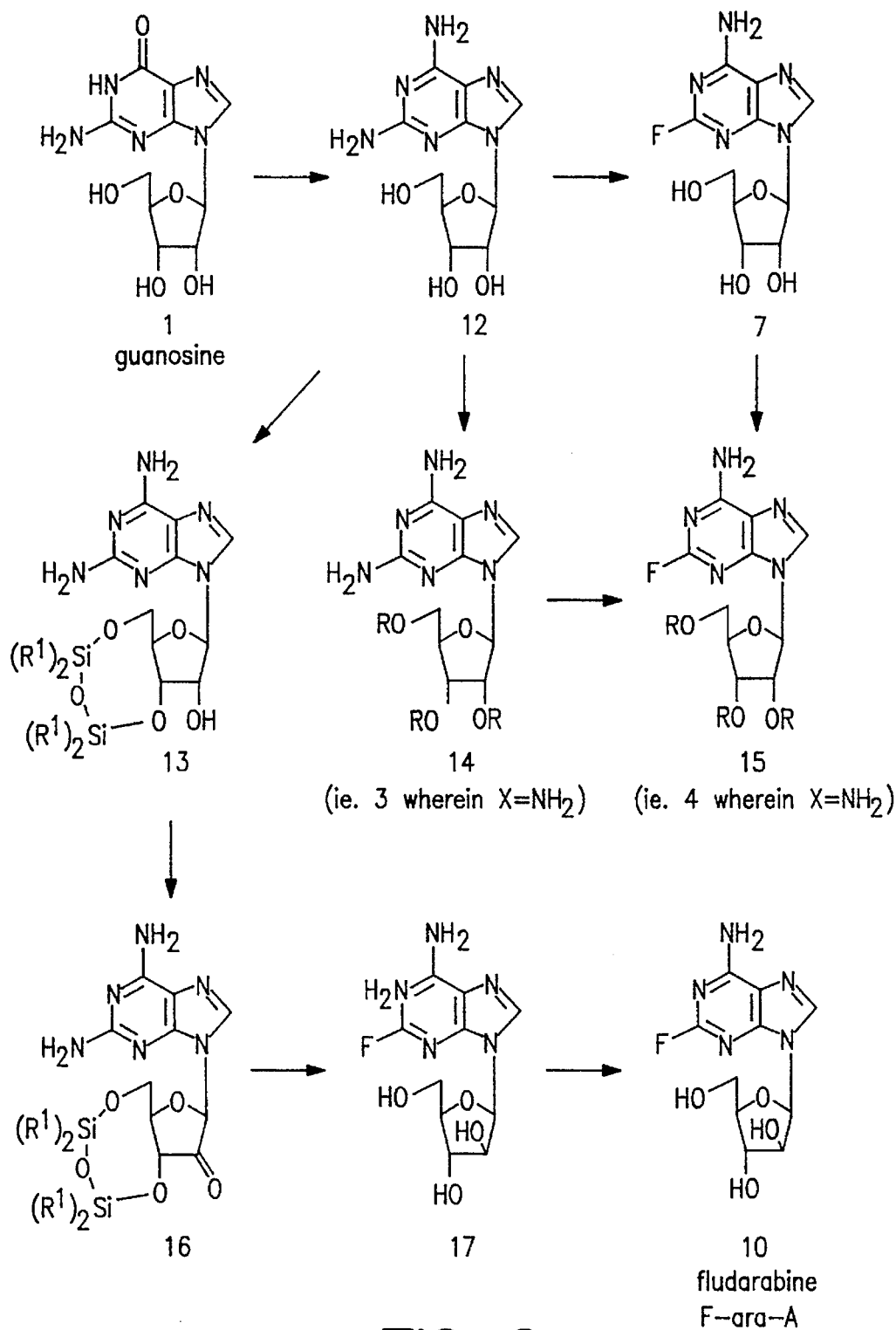
FIG. 2 (Reaction Scheme 2) illustrates an alternative general reaction procedure in accordance with the invention.

FIG. 1, or Reaction Scheme 1, illustrates a reaction process in accordance with the invention wherein the 6-keto group of guanosine is initially converted to an amino group, followed by subsequent conversion of the 2-amino group to 2-fluoro. Alternatively, conversion of the 2-amino to 2-fluoro group can be completed before complete conversion of the 6-keto group to 6-amino. Finally, the ribofuranosyl sugar moiety is converted to arabinofuranosyl.

Referring to FIG. 1, compound 1, guanosine, is initially subjected to acylation wherein the 2',3',4'-hydroxy groups are converted to acyl-O-groups, e.g., acetyl-O-, to obtain compound 2. This compound can then be subjected to a variety of reaction procedures wherein the 6-keto group is converted to a 6-X group (compound 3) wherein X is halogen, i.e., Cl, Br or F; $N_3$; $NH_2$; or $-OSO_2R^4$, wherein $R^4$ is $CH_3$, $CF_3$ or aryl optionally substituted by $C_1$–$C_4$-alkyl or $C_1$–$C_4$-alkoxy (e.g., 2,4,6-tri-isopropylphenyl).

Conversion of the 6-keto group to Cl or Br can be performed by dehydrative halogenation. The resultant 6-Cl or 6-Br compound can be converted to the 6-F by halogen exchange.

The 6-azide compound can be obtained by subjecting the 6-chloro or 6-bromo compound to reaction with an alkali metal azide, such as $LiN_3$, $NaN_3$ or $KN_3$ in a polar solvent. See also copending application Ser. No. 07/620,236, filed Nov. 29, 1990, wherein 2-amino-6-chloropurine is converted to 2-amino-6-azidopurine. To obtain compound 3 wherein X is amino, i.e., 2-aminoadenosine, the 6-azido group can be aminated using a suitable reducing agent. See, e.g., Example 3c.

Sulfonylation of the 6-keto group to obtain 6-$OSO_2R^4$ compounds can be performed in accordance with the reaction procedure disclosed by Bridson et al., J.C.S. Chem. Commun., 1977, pp. 791–792, for obtaining protected guanosine intermediates with sulfonyloxy groups in the 6-position. Compound 3, wherein X is $NH_2$, can also be obtained by subjecting the 6-Cl, 6-Br or 6-$OSO_2R^4$ to amination. In addition, the 6-$OSO_2R^4$ can be converted to 6-$NH_2$, 6-$N_3$ or 6-F using an unhindered tertiary amine such as trimethylamine or DABCO.

Conversion of the acyl-protected 2-amino-6-X compounds to the corresponding 2-fluoro compounds (compound 4) can proceed by way of diazotization and fluorination. This reaction step can be performed before or after conversion of 6-Cl, 6-Br or 6-$OSO_2R^4$ to 6-F or conversion of 6-$N_3$, 6-Cl, 6-Br, or 6-$OSO_2R^4$ to 6-$NH_2$. The resultant product is compound 4 wherein, again, R is acyl and X is Cl, Br, F, $N_3$, $NH_2$ or —$OSO_2R^4$.

To obtain compound 7 from compound 4, wherein X is Cl, Br, F or —$OSO_2R^4$, a two-step process can be utilized. Specifically, the 6-X group is initially subjected to amination and the resultant product then subjected to complete deacylation. Alternatively, for compound 4 when X is F, amination and complete deacylation can be achieved by a single-step process utilizing an alcohol solvent and ammonia. This one-step conversion process is preferred.

In the case where X is $NH_2$ in compound 4, compound 7 is produced by the single-step process of complete deacylation. On the other hand, if X is $N_3$ in compound 4, the 6-azide group is initially reduced and then the resultant compound subjected to complete deacylation to obtain compound 7.

An alternative treatment of compound 4 can be used when X is $NH_2$. The compound can be subjected to selective deacylation of the 2'-O-acyl group to achieve the partially protected 3',5'-di-O-acyl nucleoside (compound 5, wherein $R^1$ is acyl). An alternative procedure for obtaining a 3',5'-partially protected nucleoside is to subject compound 4 (X=$NH_2$) to complete deacylation, yielding compound 7, followed by subsequent formation of a disiloxane bridge between the 5'- and 3'-positions to achieve compound 5, wherein the two R' groups together are —Si(Z)$_2$—O—Si(Z)$_2$— and Z is preferably a branched $C_3$-$C_6$-alkyl or alkoxy, especially isopropyl or tert.-butyloxy, or is phenyl.

Conversion of the partially protected ribofuranosyl moiety of compound 5 to the arabinofuranosyl moiety of compound 9 can be performed by two procedures in accordance with Reaction Scheme 1. Firstly, the 2'-hydroxy group of the partially protected compound 5 can be subjected to oxo formation by oxidation to obtain compound 8. This compound is then subjected to reduction to obtain compound 9 wherein $R^3$ is H. Secondly, compound 5 can be subjected to sulfonylation wherein the 2'-hydroxy group is converted to a sulfonyloxy group of —$OSO_2R^2$, wherein $R^2$ can be, e.g., $C_{1-4}$-perfluoroalkyl or perfluorophenyl ($CF_3$ is preferred). Nucleophilic displacement of the 2'-$OSO_2R^2$ group achieves the corresponding compound with the arabinofuranosyl moiety with the group $R^3O$ in the 2'-position, wherein $R^3$ is H or acyl, i.e., compound 9. Thus, in compound 9, groups $R^1$ can be an acyl group or together can form a disiloxane bridge. $R^3$ can be either H or acyl.

Subsequent deacylation and/or desilylation produces compound 10, i.e., fludarabine. Phosphorylation of fludarabine can occur in accordance with conventional procedures to obtain the prodrug form fludarabine phosphate, i.e., compound 11.

Reaction Scheme 2 demonstrates, inter alia, procedures for converting the 2,6-diamino-unprotected compound (compound 12) by subjecting the 2,6-diamino compound to the HF-pyridine reaction discussed above and described in more detail in copending application [Attorney Docket No. SCH 1233] to obtain the resultant compound, 2-fluoroadenosine, i.e., compound 7. This compound can then be subjected to acylation to obtain the fully acyl-protected compound 2',3',5'-tri-O-acyl-2-fluoro-adenosine, i.e., compound 15. Compound 15 corresponds to compound 4 of Reaction Scheme 1, wherein X is $NH_2$. Further treatment of compound 15 to obtain fludarabine and fludarabine phosphate can proceed in accordance with the treatment of compound 4 illustrated in Reaction Scheme 1.

Conversely, the unprotected 2,6-diamino, compound 12, can be first subjected to acylation to obtain compound 14 (compound 3 of Reaction Scheme 1, wherein X is $NH_2$), followed by subsequent diazotization/fluorination to achieve the protected 2-fluoro compound (compound 15).

In addition, Reaction Scheme 2 also illustrates an alternative procedure for converting the ribofuranosyl moiety to the arabinofuranosyl moiety prior to fluorination of the 2-position. The 2,6-diamino unprotected compound is subjected to partial protection by way of a disiloxane bridge. The partially protected compound is then subjected to reduction and oxidation and deprotection to obtain compounds 16 and 17. Diazotization/fluorination of compound 17 yields fludarabine, i.e., compound 10. Hansske et al., Tetrahedron, Vol. 40, No. 1, pp. 125–135 (1984), describe conversion of the sugar moiety of compound 12 to obtain compound 17.

Figure 3:
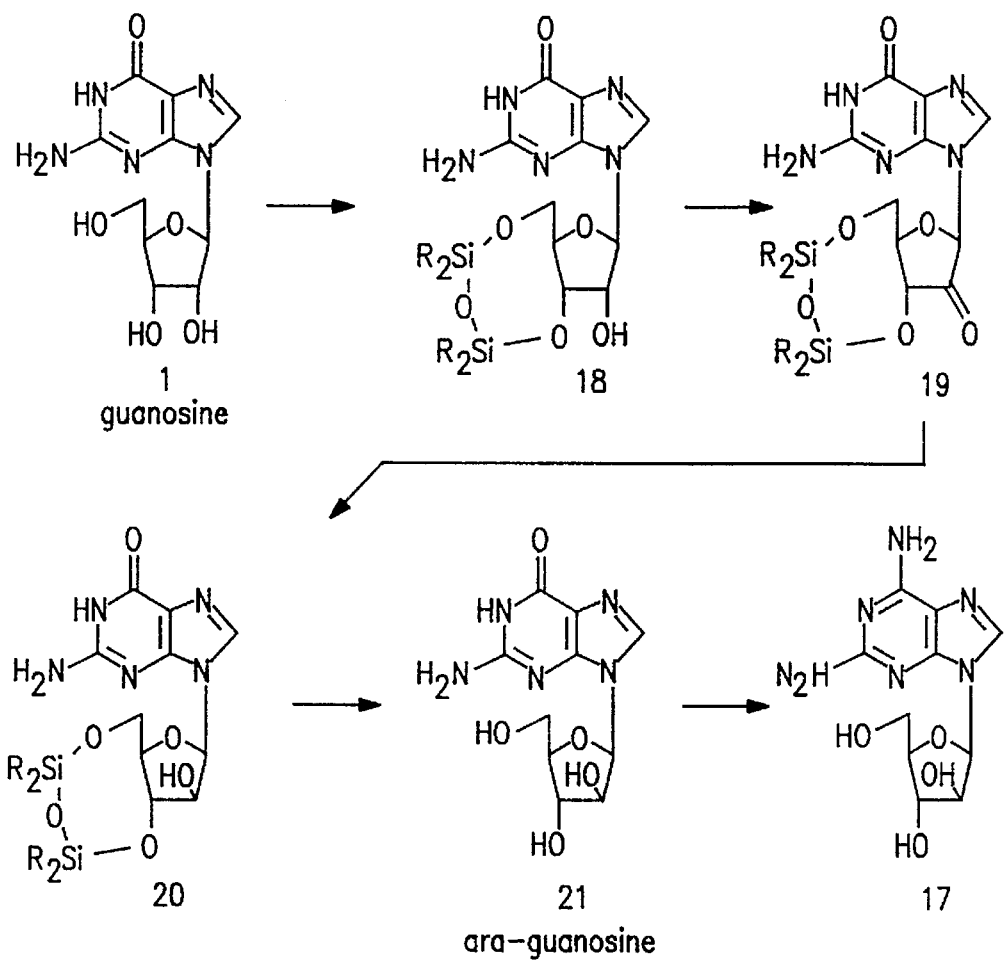
FIGS. 3 and 4 (Reaction Schemes 3 and 4) illustrate alternative procedures for performing sugar conversion of guanosine to araguanosine.

FIG. 3, Reaction Scheme 3, describes a further alternative with respect to conversion of the sugar moiety to obtain compound 17. In this procedure, guanosine is initially subjected to partial protection at the 3'- and 5'-positions by a disiloxane group. Subsequent oxidation (compound 19), reduction (compound 20) and removal of the disiloxane bridge yields ara-guanosine, i.e., compound 21. Hansske et al., Tetrahedron, Vol. 40, No. 1, pp. 125–135 (1984), also describe conversion of guanosine to ara-guanosine. Compound 17 can then be produced by, e.g., persilylation, amination and desilylation. See Vorbrüggen et al., Liebigs Ann. Chem., 1976, pp. 745–761.

Figure 4:
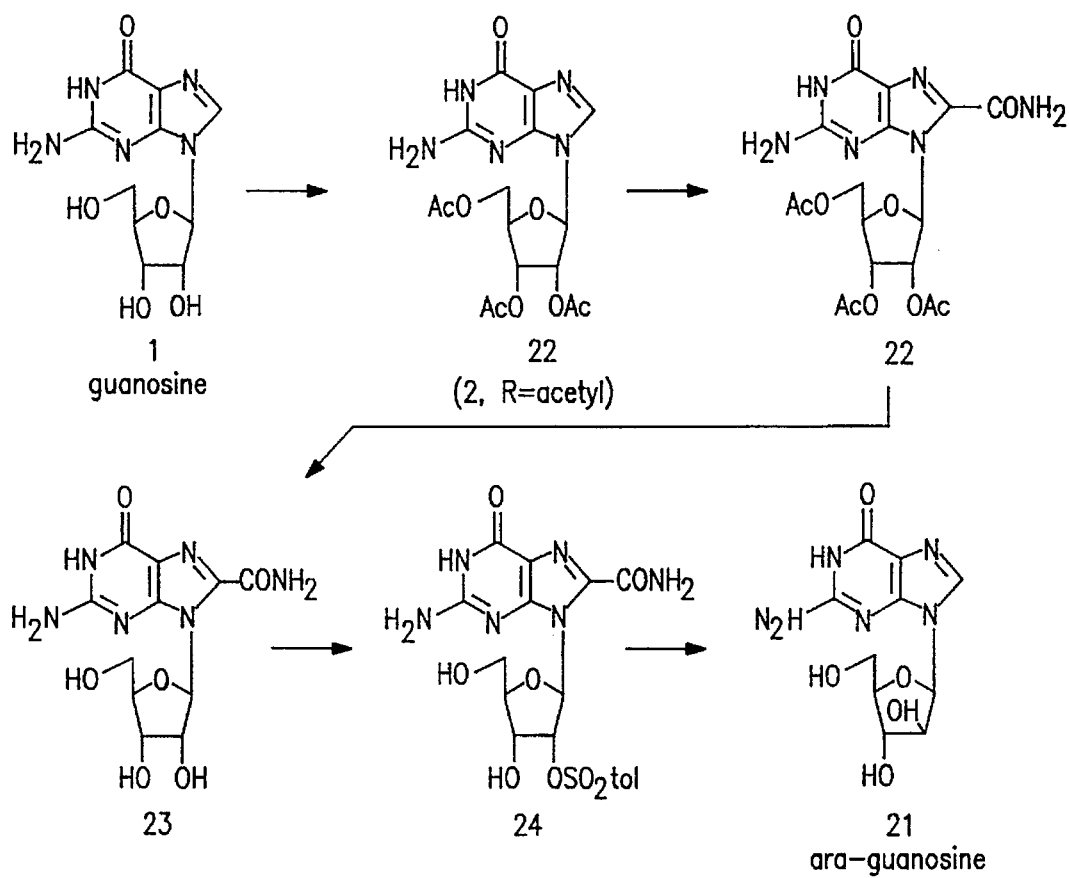
Figure 5:
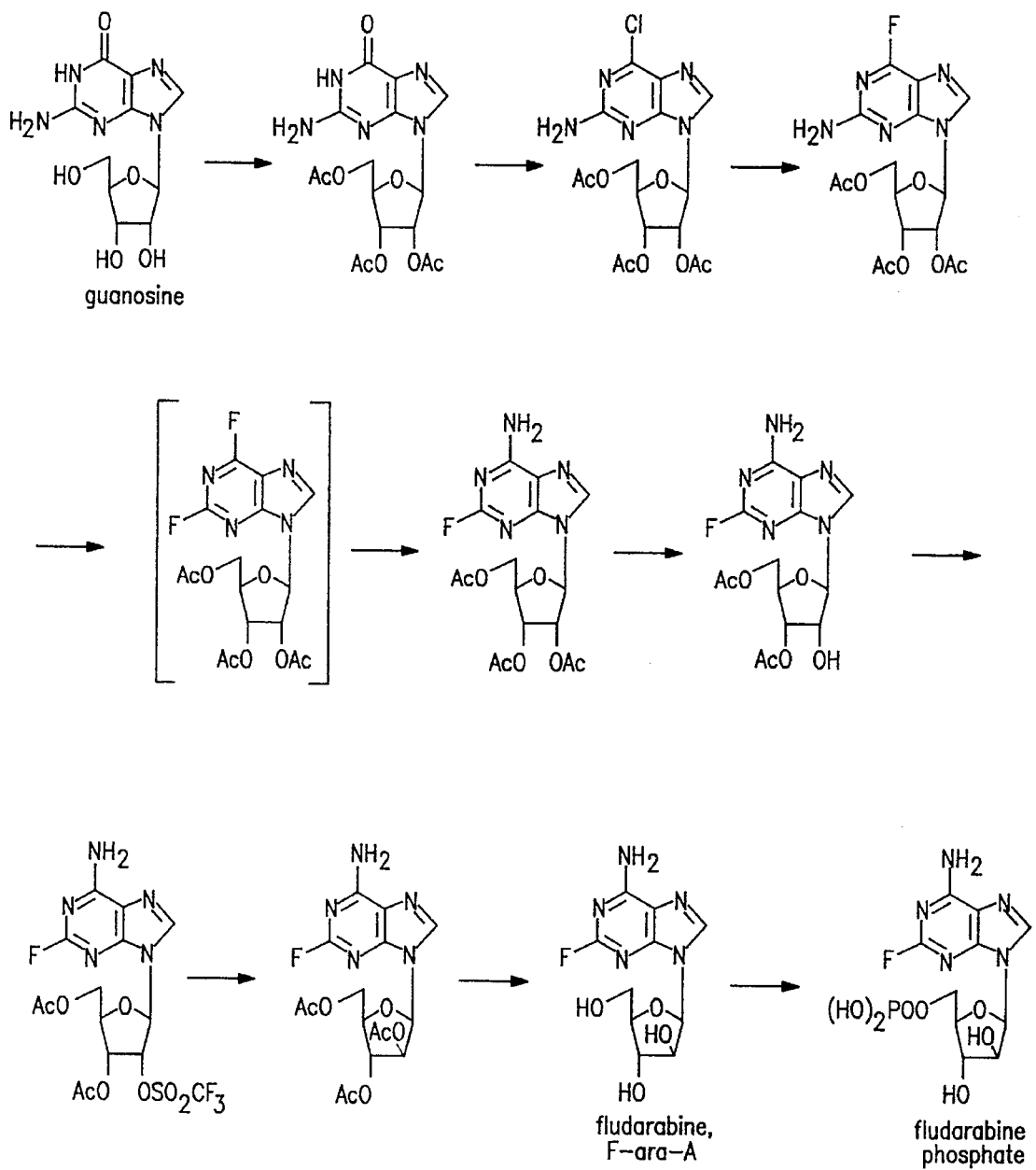
FIGS. 5, 6 and 7 (Reaction Schemes 5, 6 and 7) illustrate specific reaction procedures in accordance with the invention.

A further alternative sugar conversion procedure is illustrated in FIG. 4, i.e., Reaction Scheme 4. In this process, the fully protected compound 2',3',5'-tri-O-acyl-guanosine is converted to the corresponding 8-carbamoyl compound, i.e., compound 22. Sugar conversion is then achieved by deacylation, conversion of 2'-hydroxy to 2'-toluenesulfonyloxy and subsequent removal of the carbamoyl and toluenesulfonyloxy groups. See Timoschuk et al., Pharmaceutical Chemistry Journal, 19, pp. 259–261 (1985).

Reaction Scheme 5 shows a specific reaction procedure in accordance with general Reaction Scheme 1. Guanosine is initially subjected to acylation whereby the 2',3',5'-hydroxy groups are converted to O-acyl groups, preferably O-acetyl groups. By dehydrative halogenation, the 6-keto group is converted to 6-Cl. Subsequent halogen exchange produces the 6-fluoro-O-acyl-protected compound. The 2-fluoro-O-acyl-protected adenosine compound is obtained by diazotization/fluorination and amination. Sugar conversion then proceeds by way of selective deacylation of the 2'-O-acyl group, sulfonylation of the 2'-hydroxy group and subsequent substitution of the 2-sulfonyloxy group with a carboxylate to achieve the arabinofuranosyl moiety. Deacylation of the 2'-, 3'- and 5'-positions produces fludarabine and subsequent phosphorylation yields the prodrug form fludarabine phosphate.

Figure 6:
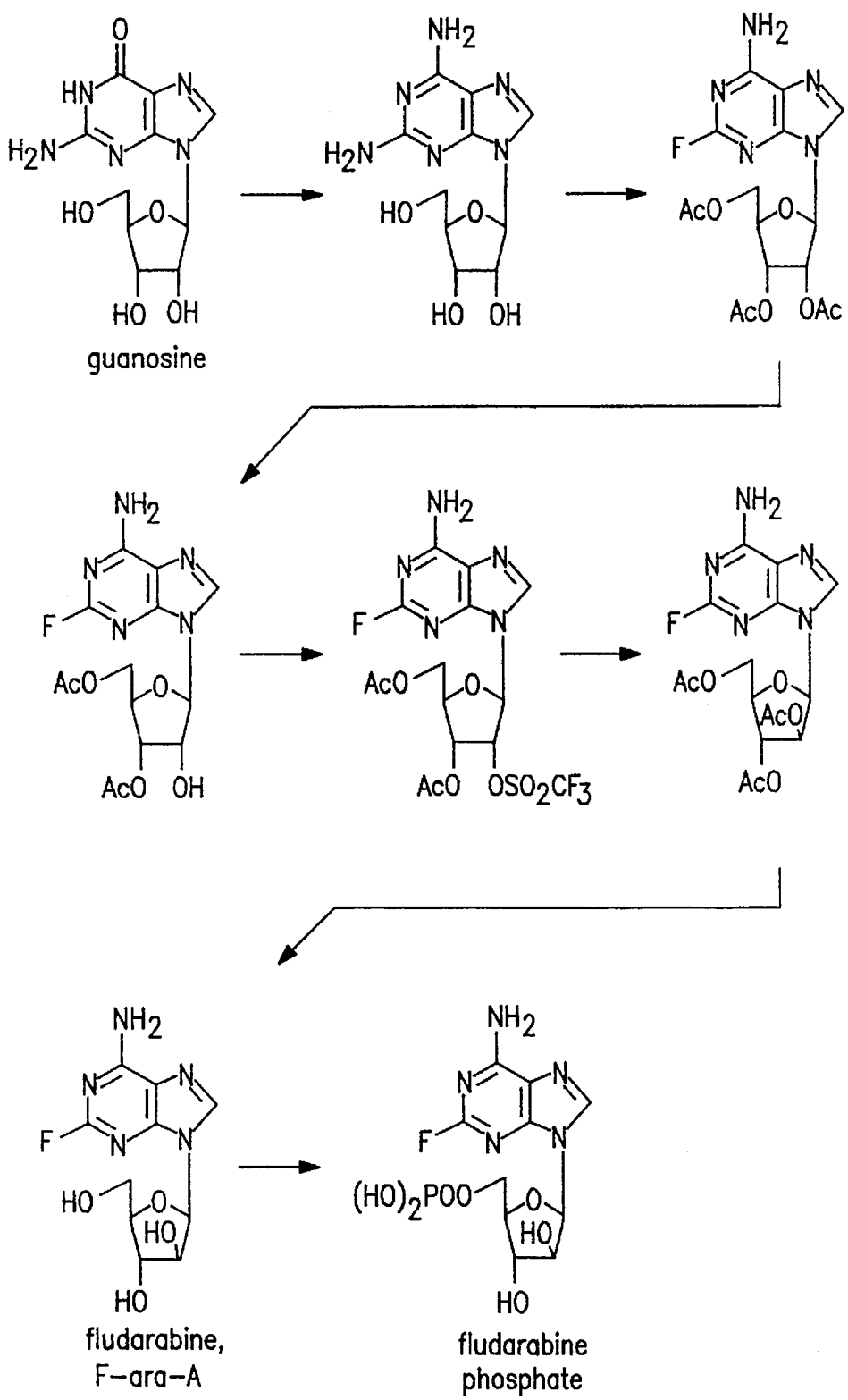

FIG. 6, i.e., Reaction Scheme 6, illustrates a particularly preferred reaction process in accordance with the present invention. Conversion of the 6-keto group is performed first, wherein guanosine is subjected to amination to obtain 2-aminoadenosine. This compound is then treated in accordance with the conversion of compound 12 to compound 15 illustrated in Reaction Scheme 2 (Ac is acyl, preferably acetyl). Selective deacylation of the 2'-position followed by sulfonylation and subsequent acylation yields 2',3',5'-tri-O-acyl-2-fluoroadenosine. Fludarabine and the prodrug form fludarabine phosphate can be obtained by deacylation and phosphorylation.

Figure 7:
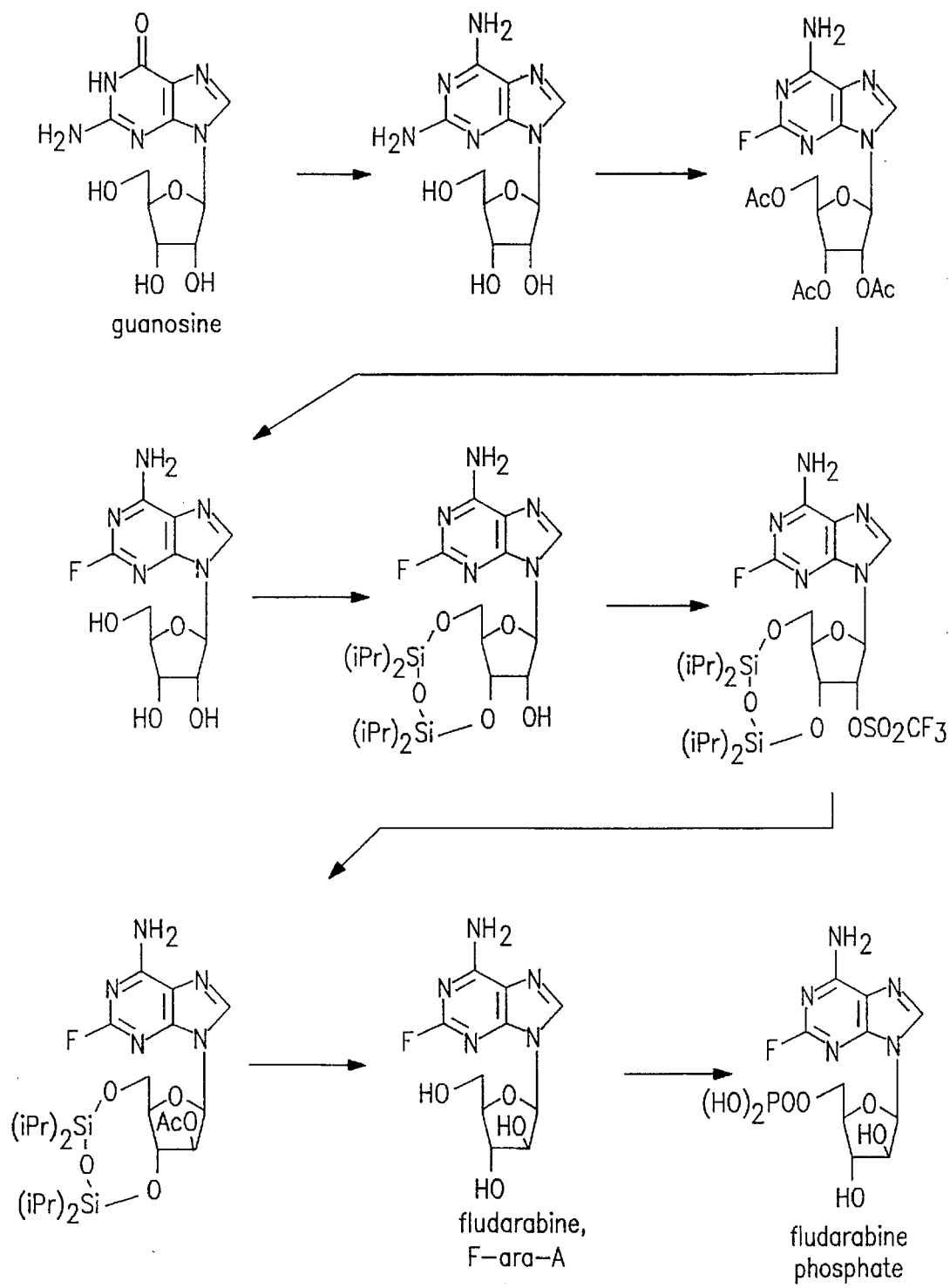

Finally, Reaction Scheme 7 (FIG. 7) demonstrates another specific reaction procedure in accordance with the invention. Amination of the 6-keto group produces the unprotected 2,6-diamino compound. Fluorination of the 2-position proceeds by way of acylation and diazotization/fluorination, or vice versa, as illustrated in the conversion of compound 12 to compound 15 in Reaction Scheme 2. Complete deacylation produces the compound 2-fluoroadenosine which is then subjected to partial protection by formation of a disiloxane bridge between the 3'- and 5'-positions. Sulfonylation of the 2'-hydroxy followed by subsequent acylation and the removal of all protecting groups produces fludarabine.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited above and below, are hereby incorporated by reference.

EXAMPLES

Example 1a: 2',3',5'-Tri-O-acetylguanosine

[Acylation]

Acetic anhydride (89.3 mL, 0.95 mol) was added rapidly to a magnetically stirred suspension of anhydrous guanosine (76.56 g, 0.27 mol), 4-dimethylaminopyridine (DMAP, 2.47 g, 0.02 mol), and triethylamine (TEA, 149 mL, 1.07 mol) in acetonitrile (500 mL, synthesis grade). The mixture was stirred magnetically, and, after a short induction period, a substantial exotherm was observed as the temperature of the mixture rose to about 50° C. Within 3–5 minutes, the mixture became a faintly cloudy solution. This solution was stirred for 30 minutes, at which time TLC (silica gel plates eluted with 6:3:1 ethyl acetate:DMF:1-butanol) showed only the title compound and a trace of $N_2$-acetyl-2',3',5'-tri-O-acetylguanosine at higher $R_f$ and DMAP at very low $R_f$.

Methanol (70 mL) was added to quench the remaining acetic anhydride, and, after stirring for 5 minutes, the mixture was concentrated under vacuum. The syrupy residue was dissolved in boiling 2-propanol (600 mL) and stirred vigorously; crystallization began almost immediately. The suspension was allowed to cool to ambient temperature, then was refrigerated. The fluffy white precipitate was collected by filtration and washed with 2-propanol. The moist solid was air dried, then dried under vacuum at 80° C. to obtain 86.5 g (78%) pure title compound. mp 228°–230° C.; $^1$H NMR (DMSO-d$_6$) δ 2.02 (s, 3H), 2.03 (s, 3H), 2.10 (s, 3H), 4.24 (dd, 1H, H-5'a), 4.30 (q, 1H, H-4'), 4.37 (dd, 1H H-5'b), 5.48 (t, 1H, H-3'), 5.78 (t, 1H, H-2'), 5.97 (d, 1H, H-1'), 6.54 (bs, 2H, NH$_2$), 7.92 (s, 1H, H-8), >9.5 (bs, 1H, NH), FT-IR (KBr) 3448, 3339, 3199, 1749, 1693, 1631, 1596, 1372, 1232, cm$^{-1}$, UV (methanol) $\lambda_{max}$ 256, 270(sh) nm.

Matsuda et al., Synthesis, 1986, pp. 385–386, disclose a process for acetylation of guanosine with acetic anhydride in acetonitrile/triethylamine and in the presence of DMAP.

Example 1b: 2',3',5'-Tri-O-acetylguanosine

[Acylation]

See Reaction Scheme 1; compound 1 to compound 2, wherein R is acetyl.

In a round-bottom flask, guanosine (87 g, 0.31 mL, predried for two days under vacuum at 100° C. over P$_2$O$_5$) was combined with acetic anhydride (180 mL, 1.9 mol), pyridine (90 mL, 1.11 mol) and N,N-dimethylformamide (DMF, 245 mL) and heated in a 75° C. oil bath. The reaction was monitored by TLC on silica gel plates eluted with 6:3:1 ethyl acetate:DMF:1-butanol. After 2 hours, the guanosine ($R_f$=0.13) was consumed and the title compound ($R_f$=0.56) was observed to be the major product.

The mixture was concentrated under vacuum. The residue was suspended in 1:1 ethyl ether:2-propanol and the solid collected by filtration. This solid was recrystallized from absolute ethanol and the product was dried at 80° C. under vacuum to obtain 106.9 g (84%) of the title compound as a fluffy white solid. mp 229°–233° C.

Robins et al., Can. J. chem., 1981, 59, pp. 2601–2607, disclose a process for acetylation of guanosine using acetic anhydride and pyridine in DMF.

Example 2: 2',3',5'-Tri-O-acetyl-6-chloroguanosine

[Dehydrative halogenation]

See Reaction Scheme 1; compound 2 to compound 3, wherein R is acetyl and X is chloro.

In a 1 L flask fitted with a magnetic stirrer, distilled phosphorous oxychloride (47.7 mL, 510 mmol) was added to a solution of dried 2',3',5'-tri-O-acetylguanosine (36.1 g, 88 mmol), benzyltriethylammonium chloride (40.2 g, 176 mmol), and N,N-dimethylaniline (11.2 mL, 88 mmol, distilled from CaH$_2$) in anhydrous acetonitrile (200 mL, distilled from P$_2$O$_5$). The flask was fitted with a reflux condenser and placed in an oil bath preheated at 100° C. The mixture was heated to reflux, and heating was continued for another ten minutes. The mixture was concentrated under vacuum, and the residue was dissolved in dichloromethane (800 mL). The solution was stirred with ice for 15 minutes before the layers were separated. The aqueous layer was then washed with several portions of dichloromethane. The combined organic extracts were washed with water and then with portions of saturated sodium bicarbonate until neutral. Finally, it was dried over MgSO$_4$, filtered, and concentrated under vacuum. The residue was recrystallized twice from 300 mL portions of 2-propanol to obtain the purified title compound. 32.2 g (85%); mp 146°–148° C.; $^1$H NMR (DMSO-d$_6$) δ 2.04 (s, 6H), 2.15 (s, 3H), 4.2–4.5 (m, 3H), 5.54 (dd, 1H), 5.88 (t, 1H), 6.11 (d, 1H), 7.07 (bs, 2H), 8.37 (s, 1H); FT-IR (KBr) 3444, 3313, 3210, 1634, 1614, 1559, 1248, 1217 cm$^{-1}$; UV (methanol) λ$_{max}$ 250, 310 nm.

Robins et al., *Can. J.Chem.*, 1981, 59, pp. 2601–2607, disclose a process for introducing a Cl atom into the 6-position of 2',3',5'-tri-O-acetylguanosine using acetonitrile, tetraethylammonium chloride, N,N-dimethylaniline and phosphorous chloride.

Example 3a: 6-Fluoro-2',3',5'-tri-O-acetylguanosine

[Halogen Exchange]

See Reaction Scheme 1; compound 3, wherein R is acetyl and X is Cl, to compound 3, wherein R is acetyl and X is F.

A 3 L, 3-neck round bottom flask fitted with a mechanical stirrer and cold finger condenser was charged with potassium fluoride (140 g, 2.4 mol, spray-dried), 2',3',5'-tri-O-acetyl-6-chloroguanosine (70 g, 0.16 mol) and anhydrous DMF (1.5 L). About 5–7 mL of trimethylamine was condensed into the flask. The suspension was stirred at ambient temperature for 24 hours and then the mixture was concentrated under vacuum. The residue was suspended in chloroform and filtered and the insoluble material was washed thoroughly with chloroform (1.5 L total). The filtrate was concentrated under vacuum and the residue was recrystallized from 2-propanol to obtain 61.7 g (92%) of the title compound. mp 143°–144° C.; $^1$H NMR (DMSO-d$_6$) δ 2.048 (s, 3H). 2.055 (s, 3H), 2.14 (s, 3H), 4.25–4.45 (m, 3H), 5.57 (dd, 1H), 5.89 (t, 1H), 6.14 (d, 1H), 7.09 (bs, 2H), 8.35 (s, 1H); $^{13}$C NMR (DMSO-d$_6$) 20.12, 20.30, 20.44, 62.91, 70.22, 71.89, 79.65, 84.95, 111.71 (d, $^2J_{CF}$=31.0 Hz, C-5), 140.94 (s, C-8), 157.07 (d, $^3J_{CF}$=11.7 Hz, C-4), 159.28 (d, $^1J_{CF}$=251.3 Hz, C-6), 159.90 (d, $^3J_{CF}$=18.2 Hz, C-2), 169.21, 169.35, 170.01 ppm; FT-IR (KBr) 3441, 3317, 3207, 1739, 1643, 1571, 1220 cm$^{-1}$; UV (ethanol) λ$_{max}$ 246, 290 nm.

Robins et al., *Can. J. Chem.*, 1981, 59, pp. 2601–2607, disclose a process for replacing the 6-Cl atom with 6-F in 2',3',5'-tri-O-acetyl-6-chloroguanosine using potassium fluoride in DMF with trimethylamine as a catalyst.

Example 3b: 6-Fluoro-2',3',5'-tri-O-acetylguanosine

[Halogen Exchange]

See Reaction Scheme 1; compound 3, wherein R is acetyl and X is Cl, to compound 3, wherein R is acetyl and X is F (with DABCO as catalyst).

A mixture of potassium fluoride (2.0 g, 34.5 mmol, spray-dried), 1,4-diazabicyclo[2.2.2]octane (13 mg, 0.12 mmol, DABCO) and 2',3',5'-tri-O-acetyl-6-chloroguanosine (1.0 g, 2.23 mmol), in anhydrous DMF (10 mL) was stirred at ambient temperature. The relative intensity of UV absorbances at 290 nm (product) and 310 nm (substrate) was monitored over time. After stirring for 2 days, the peak at 310 nm could not be detected, and the absorbance at 320 nm was negligible. The mixture was concentrated under vacuum, at 50° C. and the residue was suspended in chloroform and filtered and the insoluble material was washed thoroughly with chloroform. The filtrate was concentrated under vacuum and the residue was recrystallized from 2-propanol to obtain 0.97 g (100%) of the title compound. The UV and $^1$H NMR spectra of this material were consistent with spectra obtained for an authentic sample. $^1$H NMR (DMSO-d$_6$) δ 2.058 (s, 3H), 2.061 (s, 3H), 2.15 (s, 3H), 4.25–4.45 (m, 3H), 5.58 (dd, 1H), 5.90 (t, 1H), 6.15 (d, 1H), 7.10 (bs, 2H), 8.36 (s, 1H); UV (ethanol) λ$_{max}$ 246, 290 nm.

Example 3c: 2,6-Diamino-9-β-D-(2',3',5'-tri-O-acetylribofuranosyl)purine

[Azide Formation and Reduction]

See Reaction Scheme 1; compound 3, wherein X is Cl, to compound 3, wherein X is N$_3$, to compound 3, wherein X is NH$_2$ (R is acetyl).

A mixture of sodium azide (4.00 g, 58 mol), 2-amino-6-chloro-9-β-D-(2',3',5'-tri-O-acetylribofuranosyl)purine (10.00 g, 23.35 mmol), 1,4-diazabicyclo[2.2.2]octane (2.62 g, 23.4 mmol, DABCO), water (10 mL) and acetonitrile (100 mL) was stirred vigorously under nitrogen in the dark. After 15 minutes, TLC indicated that the reaction was about 40% complete, so additional DABCO (2.62 g, 23.4 mmol) and sodium azide (4.0 g, 58 mmol) were added. After a total of 70 minutes, TLC indicated that the reaction was complete, so the mixture was concentrated under vacuum. The residue was partitioned between chloroform (500 mL) and water. The chloroform layer was washed with water and then with sat. NaCl and then dried over Na$_2$SO$_4$, filtered and concentrated under vacuum. This provided crude 2-amino-6-azido-9-β-D-(2',3',5'-tri-O-acetylribofuranosyl)purine as a foam. The foam was dissolved in 2-methoxyethanol (150 mL) and was transferred to a hydrogenation bottle. The bottle was flushed with nitrogen, and 10% Pd/C (3.0 g) was added. The mixture was hydrogenated at 55 psi overnight. By TLC (7:3 ethyl acetate:2-propanol) the reaction was complete, so the mixture was filtered through diatomaceous earth (Celite) and the filter was washed with additional 2-methoxyethanol. The filtrate was concentrated under vacuum to obtain 8.68 g (93%) of the title compound as a foam which contained a trace of 2-methoxyethanol. This material was used without further purification. $^1$H NMR (DMSO d$_6$, 300 MHz) δ 2.06 (s, 3H), 2.07 (s, 3H), 2.14 (s, 3H), 4.25–4.50 (m, 3H, H-4',2H-5'), 5.56 (t, 1H, H-3'), 5.86 (t, 1H, H-2'), 6.06 (d, 1H, H-1'), 6.8 (bs, 2H, NH$_2$), 7.3 (bs, 2H, NH$_2$), 8.15 (s, 1H, H-8); FT-IR (KBr) 3367, 3199, 1748, 1645, 1606, 1233 cm$^{-1}$; UV (methanol) λ$_{max}$ 256, 284 nm.

Example 4a: 2-Fluoro-2',3',5'-tri-O-acetyladenosine

[Diazotization/Fluorination and Amination]

See Reaction Scheme 1; compound 3, wherein R is acetyl and X is F, to compound 4, wherein R is acetyl and X is NH$_2$.

A commercial bottle of 70% HF-pyridine (100 g, Aldrich) was equipped with a magnetic stir bar and a septum through which a teflon-coated thermometer and nitrogen line were fitted. The bottle was cooled in a dry ice/ acetone bath and anhydrous pyridine (25 mL) was added via syringe with stirring. The internal temperature was kept below 0° C. during the addition. This mixture (about 56% HF-pyridine) was transferred via syringe to a similar plastic vessel which had been fitted in the same manner and charged with 6-fluoro-2',3',5'-tri-O-acetylguanosine (17.0 g, 41.3 mmol) and cooled in an ice-salt bath. The resulting solution was kept at –0° C. to 0° C. while tert-butylnitrite (7.64 mL, 90%, 57.8 mmol) was added dropwise via syringe over a 45-minute period. The mixture was stirred an additional 15 minutes at 0° C.; then it was poured over ice (1.5 kg) in a plastic beaker with stirring. Dichloromethane (500 mL) was added and stirring was continued until most of the ice melted. The layers were separated in a glass separatory funnel and the aqueous layer was washed with two 500 mL portions of dichloromethane. The combined dichloromethane extracts were washed sequentially with 500 mL portions of 5% sodium bicarbonate, water and brine. The organic layer was then dried over $MgSO_4$, filtered and concentrated under vacuum. The residue was redissolved in toluene and concentrated under vacuum to remove any residual pyridine. This provided 14.2 g (83%) of crude 2,6-difluoro-9-α-D-(2',3',5'-tri-O-acetyl-ribofuranosyl) purine. See compound 4, wherein X is F. The oily residue was suitable for use in the next step without further purification; however, a purified sample can be obtained by careful crystallization from cold 2-propanol. $^1$H NMR (DMSO-$d_6$) δ 2.06 (s, 3H), 2.08 (s, 3H), 2.15 (s, 3H), 4.39 (dd, 1H), 4.4–4.5 (m, 2H), 5.64 (t, 1H), 5.95 (t, 1H), 6.35 (d, 1H), 8.90 (s, 1H); $^{13}$C NMR (DMSO-$d_6$) δ 20.10, 20.26, 20.33, 62.55, 69.69, 72.76, 79.76, 86.17, 119 (d, $^2J_{CF}$=30 Hz, C-5), 146.46 (t, $^4J_{CF}$=$^5J_{CF}$=2.9 Hz, C-8), 155.90 (dd, $^1J_{CF}$=215.3 Hz, $^3J_{CF}$=17.6 Hz, C-2), 156.31 (dd, $^4J_{CF}$=17.9 and 12.1 Hz, C-4), 159.78 (dd, $^1J_{CF}$=260.9 Hz, $^3J_{CF}$=18.8 Hz, C-6), 169.15, 169.31,169.93 ppm.

The crude material was dissolved in anhydrous 1,2-dimethoxyethane (250 mL) and magnetically stirred while anhydrous ammonia was bubbled through the solution. After 15 minutes, the reaction was complete as determined by TLC (silica gel plates eluted with 20:1 dichloromethane: methanol or 10:1 ethyl acetate: methanol ). The solvent was removed under vacuum and the residue was suspended in chloroform (1 L) and filtered to remove ammonium chloride. The filtrate was concentrated under vacuum and the residue was suspended in hot 2-propanol. After cooling, the solid was collected by filtration to obtain a total of 12.6 g (74% overall) of the title compound as a white solid which was a single spot by TLC. mp 201°–202° C.; $^1$H NMR (DMSO-$d_6$) δ 2.02 (s, 3H), 2.05 (s, 3H), 2.12 (s, 3H), 4.2–4.5 (m, 3H), 5.57 (t, 1H), 5.91 (t, 1H), 6.13 (d, 1H), 7.95 (bs, 2H), 8.34 (s, 1H); FT-IR (KBr) 3302, 3154, 1749, 1374, 1233 cm$^{-1}$; UV (methanol) $\lambda_{max}$ 262 nm.

Robins et al., Can. J. Chem,. 1981, 59, pp. 2608–2611, disclose a process wherein 6-fluoro-2',3',5'-tri-O-acetylguanosine is treated with tert.-butylnitrite in 60% HF/pyridine at −30° C. to obtain 2,6-difluoro-9-β-D-(2',3',5'-tri-O-acetyl-ribofuran-osyl)purine which is subsequently treated with anhydrous ammonia in dry 1,2-dimethoxyethane.

Example 4b: 2-Fluoro-2',3',5'-tri-O-acetyladenosine

[Diazotization/Fluorination and Amination]

See Reaction Scheme 1; compound 3, wherein R is acetyl and X is F, to compound 4, wherein R is acetyl and X is $NH_2$.

A solution of 6-fluoro-2',3',5'-tri-O-acetylguanosine (10.0 g, 24 mmol) in tetrahydrofuran (THF, 125 mL, reagent) was cooled to −15° C. to −10° C. and aqueous 48% fluoboric acid (13.9 mL) was added as a single portion. A solution of tert.-butylnitrite (4.17 mL, 90%, 31.6 mmol) in THF (10 mL) was added to the cooled reaction mixture over a 10-minute period. After an additional 10 minutes at −10° C., the cooling bath was removed and the mixture was warmed slowly to 40° C. in a warm water bath. The bath was removed, and the mixture was poured into a beaker containing 450 g of ice water. The product was extracted from this aqueous mixture with ethyl acetate (3×250 mL) and the combined organic phases were washed sequentially with water (2×200 mL), 5% sodium bicarbonate (3×200 mL) and brine (2×200 mL). The organic layer was then dried over $MgSO_4$ and decolorized with activated carbon. The dried solution was filtered and the solvent was evaporated under vacuum. The residue was dissolved in toluene and concentrated under vacuum. This provided 9.57 g of the difluoropurine (compound 4; wherein X is F) intermediate which was dissolved in anhydrous 1,2-dimethoxyethane and stirred while anhydrous ammonia was bubbled through the solution for 20 minutes. The mixture was then concentrated under vacuum and the residue was suspended in hot chloroform (250 mL) and filtered. The insoluble material was washed with more hot chloroform (250 mL) and the filtrates were combined and concentrated under vacuum. The residue was dissolved in 100 mL of 2-propanol which was then diluted with ethyl ether. The resulting precipitate was collected by filtration and recrystallized from 2-propanol to obtain 4.23 g (42%) of the title compound as a pale yellow solid. mp 200°–203° C.

Example 4c: 2-Fluoro-2',3',5'-tri-O-acetyladenosine

[Diazotization/Fluorination]

See Reaction Scheme 1; compound 3, to compound 4, wherein X is $NH_2$ and R is acetyl.

A polycarbonate centrifuge tube was charged with 2,6-diamino-9-β-D-(2',3',5'-tri-O-acetylribofuranosyl)purine (1.37 g, 3.36 mmol) and HF-pyridine (10 mL, about 56% HF). The mixture was stirred under a nitrogen atmosphere at ambient temperature until it became homogeneous (about 15 min). The solution was cooled to −10° C. and tert.-butyl nitrite (0.40 mL, 3.4 mmol, 90%) was added via syringe over a 1-minute period. Gas evolution became vigorous and then subsided over a 15-minute period, during which the temperature was kept below −5° C. The temperature was then allowed to warm to ambient temperature over a 45-minute period. The mixture was poured over ice and the product was extracted into chloroform (4×25 mL). The combined chloroform extracts were washed successively with 25 mL portions of sat. Cu(II)$SO_4$, water, sat. $NaHCO_3$, sat. NaCl, then dried over $MgSO_4$, filtered and concentrated under vacuum. By TLC (ethyl acetate), the residue (1.13 g) contained a mixture of the title compound and 2,6-di-fluoro-9-β-D-(2',3',5'-tri-O-acetylribofuranosyl)purine. The residue was triturated with anhydrous ethyl ether (75 mL) and the precipitate was collected by filtration, and dried to provide 0.79 g (57%) of the title compound, mp 197°–198° C., which was identical to an authentic sample by TLC, $^1$H NMR, IR, and UV. The filtrate afforded 0.35 g of oily green residue which was mostly 2,6-difluoro-9-β-D-(2',3',5-tri-O-acetylribofuranosyl)purine which can be converted to the title compound by treatment with anhydrous ammonia in an ether solvent.

This procedure, which uses a higher temperature than that employed by Robins et al., Can. J. Chem., 1981, 59, pp. 2608–2611, achieves an appreciably higher yield than the 40% disclosed therein. Therefore, a temperature range of −15° C. to +10° C. is preferred.

Example 5a: 3',5'-Di-O-acetyl-2-fluoroadenosine

[Selective Deacylation]

See Reaction Scheme 1; compound 4, wherein X is $NH_2$to compound 5, wherein R and $R^1$ are acetyl.

A mixture of 2-fluoro-2',3',5'-tri-O-acetyladenosine (8.0 g, 19.4 mmol) and anhydrous pyridine (80 mL) was stirred magnetically and warmed gently until it became homogeneous. The solution was cooled to ambient temperature and hydroxylammonium acetate (5.45 g, 58.3 mmol), which had been preweighed into a stoppered flask, was added as a single portion. The weighing flask was rinsed with pyridine (20 mL) which was added to the reaction mixture. The mixture was stirred at ambient temperatures for 2 hours; then the reaction was quenched by adding acetone (10 mL)

followed by methanol (25 mL). After 1 hour, the homogeneous mixture was concentrated under vacuum. The residue was dissolved in toluene (50 mL) and concentrated under vacuum to remove any remaining pyridine. The residue was triturated with water (150 mL) and the resulting solid was collected by filtration and washed with a small portion of ethyl ether. This provided 5.1 g of crude 3',5'-di-O-acetyl-2-fluoroadenosine which was contaminated with the 2',3',5'-tri-O-acetyl- 2',5'-di-O-acetyl-, and 5'-O-acetyl-derivatives of 2-fluoroadenosine. The crude material was dissolved in hot acetonitrile (250 mL), treated with Norit A, hot filtered and then refrigerated for 24 hours. The resulting solid was collected by filtration, washed with a small portion of ethyl ether and dried under vacuum to obtain 3.61 g (50%) of the title compound which contained a trace of 5'-O-acetyl-2-fluoroadenosine but was used in the next step without further purification. mp 209°–214° C.; $^1$H NMR (DMSO-$d_6$) δ 2.04 (s, $_3$H, CH3), 2.12 (s, 3H, CH$_3$), 4.2–4.4 (m, 3H, H-4' and 2H-5'), 4.94 (q, 1H, H-2'), 5.26 (dd, 1H, H-3'), 5.82 (d, 1H, H-1'), 5.93 (d, 1H, OH), 7.9 (bs, 2H, NH$_2$), 8.35 (s, 1H, H-8); $^{13}$C NMR (DMSO-$d_6$) 20.47, 20.68, 63.21, 70.73, 72.25, 79.37, 87.39, 117.61 (bd, $^4J_{CF}$=4.1 Hz, C-5), 140.07 (d, $^5J_{CF}$=2.8 Hz, C-8), 150.63 (bd, $^3J_{CF}$=20.5 Hz, C-4), 158.17 (d, $^3J^{CF}$=21.3 Hz, C-6), 158.56 (d, $^1J_{CF}$=204.3 Hz, C-2), 169.60, 170.06 ppm; FT-IR (KBr) 3340, 3160, 1745, 1649, 1610, 1373, 229 cm$^{31\ 1}$; FAB-MS (m/z) 370 (M+H)$^+$.

See Higuchi et al., *Anal. Chem.*, 1956, 28, 1022, regarding preparation of hydroxylammonium acetate.

Ishido et al., *J. Chem. Soc.*, P1., 1980, pp. 563–573, disclose an investigation of partial deacylation of 2',3',5'-tri-O-acyl-nucleoside Example 5b: 3',5'-Di-O-acetyl-2-fluoroadenosine

[Selective Acylation]

See Reaction Scheme 1; compound 4, wherein X is NH$_2$, to compound 5, wherein R and R$^1$ are acetyl.

2-Fluoro-2',3',5'-tri-O-acetyladenosine (30.0 g, 72.8 mmol), was added in one portion to a magnetically stirred solution of hydrazine hydrate (5.29 mL, 109 mmol assuming monohydrate, Aldrich) and glacial acetic acid (6.24 mL, 109 mmol) in anhydrous pyridine (300 mL). The homogenous mixture was stirred at ambient temperature. After 16 h, a portion was removed and quenched with acetone (1.5 mL), and this solution was analyzed by HPLC. This indicated that the reaction mixture consisted of 2-fluoro-2',3',5'-tri-O-acetyladenosine (8%), 3',5'-di-O-acetyl-2-fluoroadenosine (56%, desired product), 2',5'-di-O-acetyl-2-fluoroadenosine (22%) and 5'-O-acetyl-2-fluoroadenosine (14%). TLC (10:1 ethyl acetate:methanol) showed three main spots, the isomeric diacetyl components eluted together at R$_f$≈0.65, the starting material appeared at R$_f$≈0.73, and the monoacetate (diol) appeared at R$_f$≈0.43. At 17 h, the reaction was quenched by adding acetone (25 mL) and the mixture was stirred for 30 min. The mixture was then concentrated under vacuum and the residue was suspended in acetone (50 mL) and toluene (50 mL) and again concentrated to dryness under vacuum. The residue was washed thoroughly with water (100 mL) and the solid was collected by filtration. The wet solid was purified by suspending it in boiling acetone (100 mL) and diluting this with acetonitrile (200 mL). The acetone was allowed to boil off, then the mixture was refrigerated for 1 h at 4° C. The precipitate was collected by filtration, washed with cold acetonitrile, and was then dried under vacuum to obtain 12.5 g (46% yield) of the title compound. An additional crop of 1.04 g (4%) was obtained by partially concentrating the filtrates. By $^1$H NMR, both of these materials were consistent with authentic material.

Example 5c: 3',5'-Di-O-acetyl-2-fluoroadenosine

[Selective Deacylation]

See Reaction Scheme 1; compound 4, wherein X is NH$_2$, to compound 5, wherein R and R$^1$ are acetyl.

A suspension of hydroxylamine hydrochloride (7.58 g, 109 mmol) and anhydrous sodium acetate (8.95 g, 72.8 mmol) in anhydrous pyridine (300 mL) was stirred at ambient temperature for 30 min 2-fluoro-2',3',5'-tri-O-acetyladenosine (30.0 g, 72.8 mmol) was added in one portion to the magnetically stirred suspension. The mixture soon became homogeneous, and was stirred at ambient temperature. After 17 h, a portion was removed and quenched with acetone (1.5 mL) and this solution was analyzed by HPLC. This indicated that the reaction mixture consisted of 2-fluoro-2',3',5'-tri-O-acetyladenosine (12%, starting material), 3',5'-di-O-acetyl-2-fluoroadenosine (53%, desired product), 2',5'-di-O-acetyl-2-fluoroadenosine (23%, undesired isomer) and 5'-O-acetyl-2-fluoroadenosine (12%). At 18 h, the reaction was quenched and the mixture was processed as described in Example 5b to obtain a first crop of 13.6 g (50% yield) and a second crop of 1.45 g (5% yield). By $^1$H NMR, both of these materials were consistent with an authentic sample of 3',5'-di-O-acetyl-2-fluoroadenosine Example 5d: 3',5'-Di-O-benzoyl-2-fluoroadenosine

[Selective Deacylation]

See Reaction Scheme 1, compound 4, to compound 5, wherein X is NH$_2$ and R and R$^1$ are benzoyl.

A mixture of hydroxylammonium acetate (47 mg, 0.5 mmol) and 2-fluoro-2',3',5'-tri-O-benzoyladenosine (100 mg, 0,167 mmol) in anhydrous pyridine (2 mL) was stirred at ambient temperature for 24 hours. The excess hydroxylammonium acetate was quenched by diluting the mixture with acetone (5 mL). The mixture was then concentrated under vacuum, and the resulting residue was suspended in toluene, and the mixture was reconcentrated under vacuum. The residue was then partitioned between ethyl acetate and water and the organic layer was washed with saturated sodium chloride and then dried over magnesium sulfate. The dried solution was filtered and concentrated under vacuum and the components of the residue were separated by chromatography on a column of silica gel, by slution with a gradient starting with 1:1 dichloromethane:ethyl acetate and ending with neat ethyl acetate. The major component recovered from the column was identified as the title compound, 3',5'-di-O-benzoyl-2-fluoroadenosine, 19 mg (23% yield). $^1$H NMR δ 4.6–4.75 (m, 3H), 5.17 (q, 1H), 5.68 (dd, 1H), 5.99 (d, 1H), 6.08 (d, 1H), 7.45–7.8 (m, 6H), 7.8–8.15 (m, 6H), 8.36 (s, 1H).

Example 6a:
3',5'-di-O-acetyl-2-fluoro-2'-O-trifluoro-methanesulfonyladenosine

[Sulfonylation]

See Reaction Scheme 1; compound 5 to compound 6, wherein R$^1$ is acetyl and R$^2$ is CF$_3$.

Trifluoromethanesulfonic anhydride (1.00 mL, 5.9 mmol) was added via syringe over a 15-minute period to a stirred mixture of 3',5'-di-O-acetyl-2-fluoroadenosine (2.00 g, 5.4 mmol), DMAP (0.66 g, 5.4 mmol) and triethylamine (TEA, 0.83 mL, 5.9 mmol) in anhydrous pyridine (36 mL). After stirring for 1 hour at ambient temperature, the reaction was complete as determined by TLC (silica gel plates eluted with 10:1 ethyl acetate:methanol). The mixture was poured over ice and the product was extracted into chloroform (4×100 mL). The combined organic extracts were washed successively with water (3×100 mL) and brine (100 mL) and then dried over MgSO$_4$. The solution was filtered and the solvents were evaporated under vacuum. The residue was dissolved in toluene and concentrated under vacuum to remove any residual pyridine. This residue was dissolved in dichloromethane and filtered through silica gel with a gradient of 15–50% ethyl acetate in dichloromethane. Fractions containing the product were combined and concentrated under vacuum to obtain 2.52 g (93%) of the title compound as a light pink solid. mp 158°–159° C.; $^1$H NMR (DMSO-d$_6$) δ 2.01 (s, 3H), 2.16 (s, 3H), 4.28 (dd, 1H), 4.4–4.55 (m, 2H), 5.83 (t, 1H), 6.22 (t, 1H), 6.50 (s, 1H), 8.0 (bs, 2H), 8.38 (s, 1H); $^{13}$C NMR (DMSO-d$_6$) 20.15, 20.28, 62.07, 68.46, 78.72, 84.06, 85.03, 117.61 (bd, $J_{CF}$=4.1 Hz, C-5), 117.70 (q, $J_{CF}$=320 Hz, CF$_3$), 140.01 (d, $J_{CF}$=2.6 Hz, C-8), 150.15 (d, $J_{CF}$=20.5 Hz, C-4), 157.75 (d, $J_{CF}$=21.3 Hz, C-6), 158.51 (d, $J_{CF}$=205 Hz, C-2) ppm; FT-IR (KBr) 3333, 3188, 1753, 1650, 1375, 1219, 613 cm$^{-1}$.

Example 6b:
3',5'-Di-O-acetyl-2-fluoro-2'-O-trifluoro-methanesulfonyl-adenosine

[Sulfonylation]

See Reaction Scheme 1; compound 5 to compound 6, wherein R is acetyl and R$^2$ is CF$_3$.

Trifluoromethanesulfonic anhydride (4.08 mL, 24.3 mmol) was added via syringe over a 25-minute period to a stirred suspension of 3',5'-di-O-acetyl-2-fluoroadenosine (6.80 g, 18.4 mmol), in anhydrous pyridine (40.8 mL), cooled in an ice-water bath. The resulting solution was stirred at this temperature and monitored by TLC (neat ethyl acetate). A precipitate formed after about 20 minutes and, after 80 minutes, the reaction was complete, so the excess anhydride was quenched by adding water (1 mL). Stirring was continued for 30 minutes, then the mixture was concentrated under vacuum to a volume of about 30 mL. The thick slurry was suspended in water (68 mL) and, after standing for 1 hour at ambient temperature, the precipitated solid was collected by filtration and washed with water (2×34 mL), and air-dried to obtain 9.24 g (quantitative yield) of crude title compound. The crude product was suitable for use in subsequent reaction; however, a portion (6.0 g) was further purified by recrystallization from 2-propanol. After dissolving most of the crude material in hot 2-propanol, decolorizing carbon was added to the dark suspension and the insoluble material was removed by hot filtration. After cooling slowly to 0° C., the precipitate was collected by filtration, rinsed with 2-propanol (2×5 mL) and airdried to obtain 4.43 g of analytically pure title compound. mp 156.4°–158° C.; Anal. calcd. for C$_{15}$H$_{15}$N$_5$F$_4$O$_6$S; C, 35.93; H, 3.02; N, 13.97; F, 15.16; S, 6.39. Found: C, 35.97; H, 2.93; N, 14.07; F, 15.16; S, 6.44. By $^1$H NMR this was consistent with an authentic sample.

Example 7a: 2-Fluoro-9-β-D-(2',3',5'-tri-O-acetyl-arabinofuranosyl)adenine

[Sugar Conversion/Substitution of Sulfonate with Carboxylate]

See Reaction Scheme 1; compound 6 to compound 9, wherein R$^1$ is acetyl, R$^2$ is CF$_3$, and R$^3$ is acetyl.

A solution of potassium acetate (78 mg, 0.8 mmol) in water (50 μL) was added to a solution of 3',5'-di-O-ace-tyl-2-fluoro-2'-O-trifluoromethanesulfonyladenosine (0.20 g, 0.40 mmol) in N,N-dimethylformamide (500 μL) and the mixture was warmed to about 50° C. After standing at this temperature for 15 hours, TLC (ethyl acetate) showed that the reaction was complete. The mixture was cooled to ambient temperature and was diluted with water (2 mL). A precipitate formed, and this was collected by filtration, washed with methanol (2×1 mL) and air-dried to obtain 0.10 g (60% yield) of the title compound. By $^1$H NMR this was consistent with an authentic sample.

Example 7b: 2-Fluoro-9-β-D-(2',3',5'-tri-O-acetyl arabinofuranosyl)adenine

[Sugar Conversion/Substitution of Sulfonate with Carboxylate]

See Reaction Scheme 1; compound 6 to compound 9, wherein R$^1$ is acetyl, R$^2$ is CF3, and R$^3$ is acetyl.

N,N-Diisopropylethylamine (2.10 mL, 12.1 mmol) was added to a mixture of 3',5'-di-O-acetyl-2-fluoro-2'-Otrifluoromethanesulfonyladenosine (2.02 g, 4.02 mmol) and glacial acetic acid (0.92 mL, 16.1 mmol) in ethyl acetate (40 mL) and the mixture was heated to reflux under a nitrogen atmosphere. The reaction was monitored by TLC (silica gel plates eluted with ethyl acetate) and was complete after 24 hours at reflux. The mixture was cooled and diluted with ethyl acetate and then washed successively with water, 5% sodium bicarbonate and brine and then dried over MgSO$_4$. The solution was filtered and concentrated under vacuum to obtain 1.56 g (94%) of the crude title compound. Recrystallization from absolute ethanol provided 1.33 g (80%) of the title compound as needles, mp 182°–183° C.; $^1$H NMR (DMSO-d$_6$) δ 1.79 (s, 3H), 2.04 (s, 3H), 2.12 (s, 3H), 4.2–4.45 (m, 3H), 5.56 (t, 1H), 5.60 (t, 3H), 6.42 (d, 1H), 7.9 (bs, 2H), 8.21 (s, 1H); FT-IR (KBr) 3315, 3155, 1748, 1666, 1610, 1370, 1228, 1051 cm$^{-1}$.

Example 7c:
9-β-D-(3',5'-Di-O-acetyl-2'-O-propionyl arabinofuranosyl)-Z-fluoroadenine

[Sugar Conversion/Substitution of Sulfonate with Carboxylate]

See Reaction Scheme 1; compound 6 to compound 9, wherein R$^1$ is acetyl, R$^2$ is CF3, and R$^3$ is propionyl.

A mixture of 3',5'-di-O-acetyl-2-fluoro-2'-O-trifluoromethanesulfonyladenosine (0.60 g, 1.2 mmol) and cesium propionate-propionic acid (0,672 g, 2.4 mmol) in anhydrous N,N-dimethylformamide (1.5 mL) was stirred at ambient temperature. After 24 hours, TLC (ethyl acetate) showed that the reaction was complete. The mixture was diluted with water (5 mL), with vigorous stirring, and the resulting precipitate was collected by filtration. The filter cake was washed with water (2×2 mL) and airdried to afford 0.36 g (67% yield) of the title compound as an off-white powder. By $^1$H NMR, this sample was pure, except for a trace of DMF. A sample of the title compound, purified by recrystallization from ethanol, had the following characteristics. mp 159°–160° C. $^1$H NMR (DMSO-d$_6$, 300 MHz) δ 0.69 (t, 3H), 1.9–2.25 (m, 2H), 2.04 (s, 3H), 2.11 (s, 3H), 4.25–4.45 (m, 3H), 5.5–5.7 (m, 2H), 6.43 (d, 1H), 7.9 (bs, 2H), 8.20 (s, 1H); FT-IR (KBr) 3334, 3184, 1747, 1648, 1609, 1370, 1226 cm$^{-1}$; UV (methanol) λ$_{max}$ 262 nm.

Example 7d:
9-β-D-[3',5'-di-O-acetyl-2'-O-(4-nitro-benzoyl)arabinofuranosyl]-2-fluoroadenine

[Sugar Conversion/Substitution of Sulfonate with Carboxylate]

See Reaction Scheme 1; compound 6 to compound 9, wherein R$^1$ is acetyl, R$^2$ is CF$_3$, and R$^3$ is 4-nitrobenzoyl.

Triethylamine (0.112 mL, 0.8 mmol, TEA), 4-nitrobenzoic acid (0.167 g, 1.0 mmol) and 3',5'-di-O-acetyl-2-fluoro-2'-O-trifluoromethanesulfonyladenosine (0.20 g, 0.40 mmol) were combined in N,N-dimethylformamide (500 μL) and heated at 55° C. for 2 hours. Additional TEA (0.15 mL) was added and the mixture was diluted with water (2 mL) and mixed vigorously. The resulting precipitate was collected by filtration, and was washed with water (2×2 mL) and air-dried to obtain 0.18 g (87% yield) of the title compound. By $^1$H NMR, the product was pure, except for traces of DMF and 4-nitrobenzoic acid. $^1$H NMR (DMSO-$d_6$, 300 MHz) δ 2.04 (s, 3H), 2.11 (s, 3H), 4.35–4.5 (m, 3H), 5.84 (t, 1H), 5.91 (t, 1H), 6.58 (d, 1H), 7.82 (bs, 2H), 7.89 (d, 2H), 8.23 (d, 2H), 8.30 (s, 1H).

Example 8a: 9-β-D-Arabinofuranosyl-2-fluoro-adenine (fludarabine)

[Complete Deacylation]
See Reaction Scheme 1; compound 9, wherein $R^1$ and $R^3$ are acetyl, to compound 10.

A suspension of 2-fluoro-9-β-D-(2',3',5'-tri-O-acetylarabinofuranosyl)adenine (1.27 g, 3.08 mol) in absolute ethanol (130 mL) was magnetically stirred and cooled to 0° C. in an ice-brine bath under nitrogen. Anhydrous ammonia was bubbled through the suspension until it became homogeneous (30 minutes). The flask was then sealed with a septum and placed in a refrigerator at 0°–4° C. After four days, the mixture was concentrated under vacuum. The residue was triturated with chloroform to yield 0.88 g of powder which consisted of a 3:1 molar ratio complex of the title compound and acetamide. This was recrystallized from 25 mL of 50% aqueous ethanol. The resulting solid was collected by filtration, washed with aqueous ethanol, air-dried overnight and then dried at 100° C. under vacuum over $P_2O_5$ to obtain 0.75 g (85%) of pure fludarabine in its anhydrous form. mp 252°–254° C.; $^1$H NMR (DMSO-$d_6$) δ 3.6–3.75 (m, 2H, 2H-5') 3.77 (q, 1H, H-4'), 4.05–4.2 (m, 2H, H-2', and H-3'), 5.07 (t, 1H, 5'-OH), 5.52 (d, 1H, OH), 5.63 (d, 1H, OH), 6.11 (d, 1H, H-1'), 7.8 (bs, 2H, NH$_2$), 8.17 (s, 1H, H-8); FT-IR (KBr) 3455, 3308, 3185, 1641, 1378 cm$^{-1}$.

Example 8b: 9-β-D-Arabinofuranosyl-2-fluoroadenine (fludarabine)

[Complete Deacylation]
See Reaction Scheme 1; compound 9, wherein $R^1$ is acetyl and $R^3$ is propionyl, to compound 10.

Lithium hydroxide monohydrate (84 mg, 2.0 mmol) as added to a solution of 9-β-D-(3',5'-di-O-acetyl-2'-O-propionylarabinofuranosyl)-2-fluoroadenine (0.21 g, 0.50 mmol) in a mixture of tetrahydrofuran (5 mL) and water (1 mL). The mixture was stirred at ambient temperature and monitored by TLC (9:1 chloroform:methanol). After 2 hours, the reaction was complete, so the mixture was neutralized with glacial acetic acid (29 μL, 0.5 mmol) and was concentrated under vacuum to about 1 mL, and a fine precipitate formed. The mixture was allowed to stand at ambient temperature for about 30 min. and then the precipitate was collected by filtration and washed with water (2×1 mL). The collected solid was air dried to obtain 0.13 g (90% yield) of hydrated fludarabine as an off-white powder. This was a single spot by TLC, and was consistent with an authentic sample of fludarabine.0.25 H$_2$O by IR, TLC and $^1$H NMR. mp 247°–249° C. (d). FT-IR (KBr) 3475, 3387, 3128, 1672, 1621, 1382, 1057 cm$^{-1}$.

Example 8c: 9-β-D-Arabinofuranosyl-2-fluoroadenine (fludarabine)

[Complete Deacylation]
See Reaction Scheme 1 compound 9, wherein $R^1$ is acetyl and $R^3$ is 4-nitrobenzoyl, to compound 10.

A solution of 2.5 N sodium hydroxide (0.35 mL, 0.875 mmol) was added dropwise with stirring to an ice-water cooled solution of 9-β-D-[3',5'-di-O-acetyl-2'-O-(4-nitrobenzoyl)arabinofuranosyl]-2-fluoroadenine (0.104 g, 0.20 mmol) in a mixture of tetrahydrofuran (2 mL) and water (0.2 mL). The mixture was stirred in an ice-water bath and monitored by TLC (9:1 chloroform:methanol). After 1 hour, the reaction was complete, so the mixture was neutralized with glacial acetic acid (17 μL) and was concentrated to dryness under vacuum. The residue was slurried with water (1 mL) and then centrifuged. The supernatant liquid was decanted and the moist residue was recrystallized from 50% aqueous ethanol (1.6 mL). The resulting precipitated was collected by filtration and washed with ethanol (0.5 mL) and air dried to obtain 28 mg (48% yield) of hydrated fludarabine as a white powder. mp 254°–255° C. (d). This was a single spot by TLC and was consistent with an authentic sample by IR, TLC and $^1$H NMR.

Example 9a: 2-Fluoroadenosine

[Complete Deacylation]
See Reaction Scheme 1; compound 4 to compound 7, wherein X is NH$_2$ and $R^1$ is acetyl.

Anhydrous ammonia was bubbled through a magnetically stirred suspension of 2-fluoro-2',3',5'-tri-O-acetyl-adenosine (2.10 g, 5.1 mmol) in absolute ethanol (500 mL) cooled in an ice-water bath. After 30 min the mixture became homogenous so the addition of ammonia was stopped. The container was tightly stoppered and was stored at 4° C. for days, then the mixture was concentrated under vacuum. The residue was recrystallized twice from ethanol and dried to obtain 1.32 g (90%) of the title compound. $^1$H NMR (DMSO-$d_6$, 300 MHz) δ 3.5–3.75 (m, 2H), 3.96 (q, 1H), 4.15 (q, 1H), 4.54 (q, 1H), 5.09 (t, 1H), 5.32 (d, 1H), 5.50 (d, 1H), 5.81, (d, 1H), 7.9 (bs, 2H), 8.38 (s, 1H); FT-IR (KBr) 3323, 1688, 1617, 1368 cm$^{-1}$; UV (ethanol) $\lambda_{max}$ 262 nm.

See Montgomery et al., J. Org. Chem., 1968, 33, pp. 432–434.

Example 9b: 2-Fluoroadenosine

[Complete Deacylation]
See Reaction Scheme 1; compound 4 to compound 7, wherein X is NH$_2$ and $R^1$ is acetyl.

2-Fluoro-2',3',5'-tri-O-acetyladenosine (0.41 g, 10 mmol) was dissolved in a mixture of 1,4-dioxane (7 mL) and water (2 mL) and the solution was cooled in an ice-water bath. 2.5 M NaOH (1.40 mL, 3.5 mmol) was added dropwise with vigorous stirring over a 2 min. period. The resulting bright yellow solution was stirred at 0° C. and monitored by TLC (9:1 Chloroform:methanol). After 2 hours, most of the yellow color had faded and TLC showed no acetylated intermediates remaining. The homogeneous reaction mixture was poured directly onto a column of AG 50-X4 (H$^+$, 100–200 mesh, 10 mL bed volume) ion exchange resin and the column was eluted with several column volumes of 1:1 methanol:water. 2-Fluoroadenosine began to elute immediately, and all fractions which contained 2-fluoroadenosine were concentrated under vacuum to obtain a white partially crystalline solid which was dried overnight at 60° C. under vacuum: 0.20 g (70% yield), mp 220°–227° C. (d). This material was consistent by TLC, IR and UV with an authentic sample of 2-fluoroadenosine.

Example 9c: 2-Fluoroadenosine

[Complete Deacylation]
See Reaction Scheme 1; compound 4 to compound 7, wherein X is NH$_2$ and $R^1$ is acetyl.

2-Fluoro-2',3',5'-tri-O-acetyladenosine (0.41 g, 1.0 mmol, lt. yellow solid) was dissolved in a mixture of 1,4-dioxane (5 mL) and water (1 mL) . The solution was stirred at ambient temperature and solid LiOH·H$_2$O (1.40 mL, 3.5 mmol) was added in one portion. The progress of the reaction was monitored by TLC (9:1 Chloroform:methanol). After 2 hours, most of the suspended solid had dissolved and TLC showed no acetylated intermediates remaining. The cloudy reaction mixture was poured directly onto a column of AG 50-X4 (H$^+$, 100–200 mesh, 10 mL bed volume) ion exchange resin and the column was eluted with several column volumes of 1:1 methanol:water. 2-Fluoro-adenosine began to elute immediately, and all fractions which contained 2-fluoroadenosine were concentrated under vacuum to obtain a white partially crystalline solid which was dried overnight at 60° C. under vacuum: 0.18 g (63% yield), mp 227°–230° C. (d). This material was consistent by TLC, IR and UV with an authentic sample of 2-fluoroadenosine.

Example 10:
2-Fluoro-3',5'-O-(1,1,3,3-tetraiso-propyl-disiloxane-1,3-diyl)adenosine

[Selective Disiloxane Protection]

See Reaction Scheme 1; compound 7 to compound 5, wherein R$^1$ is —Si(isopropyl)$_2$—O—Si(isopropyl)$_2$—.

To a magnetically stirred suspension of dried 2-fluoroadenosine (3.00 g, 10.5 mmol) in anhydrous pyridine (100 mL) was added 1,3-dichloro-1,1,3,3-tetraisopropyldisiloxane (3.36 mL, 10.5 mmol, Aldrich) via syringe. The mixture was stirred under nitrogen for 3 h at ambient temperature, then concentrated under vacuum. The residue was twice suspended in toluene and reconcentrated under vacuum. The residue was partitioned between ethyl acetate and water and the organic layer was washed successively with 1N HCl (2X), sat. NaHCO$_3$, sat. NaCl and then dried over Na$_2$SO$_4$. The solution was filtered and concentrated under vacuum. This provided 2.56 g (46%) of the title compound, mp 200°–205° C. Additional crops of 1.11 g, (20%, mp 195°–200° C.) and 0.62 g (11%, mp 194°–200° C.) were recovered from the mother liquors. $^1$H NMR (DMSO-d$_6$, 300 MHz) δ 0.6–1.3 (m, 21H), 3.9–4.1 (m, 3H), 4.51 (t, 1H), 4.71 (dd, 1H), 5.62 (d, 1H), 5.79 (s, 1H), 7.85 (bs, 2H), 8.18 (s, 1H); FT-IR (KBr) 3333, 3188, 2946, 2869, 1649, 1606 cm$^{-1}$; UV (methanol) λ$_{max}$ 262 nm.

Example 11:
2-Fluoro-3',5',-O-(1,1,3,3-tetraisopropyl-disiloxane-1,3diyl)-2'-O-(trifluoro-methanesufonyl)adenosine

[Sulfonylation]

See Reaction Scheme 1; compound 5 to compound 6, wherein R$^1$ is —Si(isopropyl)$_2$—O—Si(isopropyl)$_2$— and R$^2$ is CF$_3$.

Trifluoromethanesulfonic anhydride (0.70 mL, 4.2 mmol) was added via syringe with magnetic stirring to a solution of 2-Fluoro-3',5'-O-(1,1,3,3-tetraisopropyl-disiloxane-1,3-diyl)adenosine (2.00 g, 3.79 mmol), triethylamine (0.58 mL, 4.2 mmol) and 4-dimethylaminopyridine (0.46 g, 3.8 mmol) in anhydrous dichloromethane (65 mL) at ambient temperature under a nitrogen atmosphere. The mixture was stirred for 1.5 h, then it was poured over ice and the product was extracted into dichloromethane (3×100 mL). The combined dichloromethane extracts were washed with water (2×250 mL) and then with sat. NaCl, then dried over MgSO$_4$, filtered and concentrated under vacuum. The product was purified by silica gel (60 g) chromatography using a gradient from 100% dichloromethane to 100% ethyl acetate. This provided 1.39 g (55%) of the title compound as an orange solid which was not purified further. mp 160°–161° C., $^1$H NMR (DMSO-d$_6$, 300 MHz) δ 0.8–1.2 (m, 21H), 3.9–4.15 (m, 3H), 5.22 (dd, 1H), 6.02 (d, 1H), 6.42 (s, 1H), 8.0 (vbs, 2H), 8.22 (s, 1H); FT-IR (KBr) 3329, 3187, 2949, 2871, 1650, 1605 cm$^{-1}$.

Example 12:
9-β-D-[2'-O-Acetyl-3'5'-O-(1,1,3,3-tetra-isopropyldisiloxane-1,3-diyl)arabinofurano-syl]-2-fluoroadenine

[Sugar Conversion/Substitution of Sulfonate with Carboxylate]

See Reaction Scheme 1; compound 6 to compound 9, wherein R$^1$ is —Si(isopropyl)$_2$—O—Si(isopropyl)$_2$—, R$^2$ is CF$_3$ and R$^3$ is acetyl.

A mixture of 2-fluoro-3',5'-O-(1,1,3,3-tetraiso-propyldisiloxane-1,3-diyl)-2'-O-trifluoromethanesulfonyl)adenosine (0.31 g, 0.47 mmol), glacial acetic acid (0.11 mL, 1.9 mmol), N,N-diisopropylethylamine (0.25 mL, 1.4 mmol) and ethyl acetate (6.0 mL) was heated at reflux. After 24 h additional acetic acid (0.11 mL, 1.9 mmol) and N,N-diisopropylethylamine (0.25 mL, 1.4 mmol) were added and heating was continued. After an additional 24 h the mixture was cooled and diluted with ethyl acetate. The solution was washed several times with 5% NaCO$_3$, then with sat. NaCl and then dried over MgSO$_4$. The solution was filtered and concentrated under vacuum to obtain 0.25 g (93%) of the title compound as a yellow oil which was not purified further. $^1$H NMR (DMSO-d$_6$, 300 MHz) δ 0.7–1.4 (m, 21H), 1.65 (s, 3H), 3.9–4.0 (m, 2H), 4.19 (dd, 1H), 4.98 (t, 1H), 5.56 (t, 1H), 6.33 (d, 1H), 7.9 (bs, 2H), 8.05 (s, 1H); FT-IR (neat) 3334, 3190, 2947, 2869, 1750, 1649, 1606 cm$^{-1}$.

Example 13: 2-Fluoro-9-β-D-arabinofuranosyl-adenine (fludarabine)

[Complete Deprotection: Desilylation and Deacylation]

See Reaction Scheme 1; compound 9, wherein the two R$^1$groups together are —Si(isopropyl)$_2$—O—Si(isopropyl)$_2$— and R$^3$ is acetyl, to compound 10.

Tetrabutylammonium fluoride (0.84 mL, 0.84 mmol, 1M in THF, Aldrich) was added via syringe to a solution of 2-fluoro-9-β-D-[2'-O-acetyl-3',5'-O-(1,1,3,3-tetraiso-propyldisiloxane-1,3-diyl)arabinofuranosyl]adenine (0.24 g, 0.42 mmol) in tetrahydrofuran (4 mL, THF). After 15 min the mixture was concentrated under vacuum. The residue was taken up in hot 50% aqueous ethanol and the solution was allowed to cool. After cooling to ambient temperature, the solution was filtered and the filtrate was concentrated under vacuum. This residue was partitioned between ethyl acetate and water. The aqueous layer was washed with ethyl acetate and the combined organic extracts were dried over MgSO$_4$, then filtered and concentrated under vacuum. This left a solid residue (0.12 g) which by $^1$H NMR contained 2'-O-acetyl-F-ara-A along with some tetrabutylammonium salt and isopropylsilyl by-products. $^1$H NMR (DMSO-d$_6$, 300 MHz) δ 1.73 (s, 3H), 3.6–3.8 (m, 2H), 3.8–3.9 (m, 1H), 4.39 (q, 1H), 5.07 (t, 1H), 5.27 (t, 1H), 5.84 (d, 1H), 6.31 (d, 1H), 7.85 (bs, 2H), 8.24 (s, 1H).

A portion of the crude intermediate (0.10 g) was suspended in absolute ethanol (50 mL) and cooled in an ice bath. Anhydrous ammonia was bubbled through the suspension until it became homogeneous. The solution was then stored at 4° C. for three days, then concentrated under vacuum. The residue was recrystallized from 50% aqueous ethanol. The precipitate was collected by filtration and dried under vacuum at 90° C. to obtain 26.9 mg (about 27% yield for two steps after correction for samples) of fludarabine, mp 256° C. (decomp.), which was identical to an authentic sample by TLC, $^1$H NMR and IR.

Example 14:
9-β-D-(3',5'-Di-O-acetylarabino-furanosyl)-2-fluoroadenine

[Oxidation/Reduction]

See Reaction Scheme 1; compound 5 to compound 8 to compound 9, wherein $R^1$ is acetyl and $R^3$ is H.

A mixture of 3',5'-di-O-acetyl-2-fluoroadenosine (0.148 g, 0.4 mmol), chromium (VI) oxide (0.120 g, 1.2 mmol), pyridine (0.20 mL) and acetic anhydride (0.12 mL) in dichloromethane (3.0 mL) was stirred for 1 hour at ambient temperature The reaction mixture was poured directly onto a silica gel column and the intermediate 2'-keto product was eluted as a single fraction with ethyl acetate After concentration of the eluate under vacuum, the residue was dissolved in toluene and reconcentrated By $^1$H NMR, the intermediate sample was a mixture of the 2'-keto compound and the corresponding ketone hydrate (i.e., 2',2'-diol) A portion of this mixture was dissolved in glacial acetate (2 mL) and sodium borohydride (84 mg, 0.4 mmol) was added After about 24 hours, the mixture was concentrated to dryness under vacuum The residue was partitioned between ethyl acetate and water The ethyl acetate extract was washed sequentially with water, saturated sodium bicarbonate, saturated NaCl, and concentrated under vacuum. The residue was subjected to silica gel chromatography, with gradient elution with dichloromethane containing 0–100% ethyl acetate to obtain 20 mg of the title compound $^1$H NMR (DMSO-$d_6$) δ 2.03 (s, 3H), 2.12 (s, 3H), 4.1–4.2 (m, 1H), 4.30 (dd, 1H), 4.35–4.5 (m, 2H), 5.22 (t, 1H), 6.15–6.2 (m, 2H), 7.9 (bs, 2H), 8.15 (s, 1H); FT-IR (KBr) 3330, 3180, 1743, 1653, 1611, 1372, 127 cm$^{-1}$; UV (methanol) $\lambda_{max}$ 260 nm.

Example 15: 2-Fluoro-2',3',5'-tri-O-acetyladenosine

[Diazotization/Fluorination and Acylation]

See Reaction Scheme 2; compound 12 to compound 7 to compound 15, wherein R is acetyl Cold 56% HF-pyridine (20.0 mL, 24.3 g) was added rapidly via syringe to a 100 mL plastic bottle which had been charged with 2-aminoadenosine (4.80 g, 17.0 mmol) and equipped with a 1" magnetic spin bar with a teflon-coated thermometer and a nitrogen line were fitted through the rubber septum. The mixture was stirred without external cooling until it became homogeneous the solution was cooled to −15° C. and tert-butylnitrite (2.50 mL, 18.9 mmol, 90%) was added via syringe over a 20 min. period with the internal temperature maintained at −10° C.—15° C. The reaction was stirred at −10° C.—12° C. for 40 min., then the mixture was cooled to −15° C. and anhydrous pyridine (16.6 mL, 0.205 mol) was added via syringe. The internal temperature was kept below −10° C. during the first quarter of the addition, then was allowed to rise to 0° C. during the remainder of the addition. Acetic anhydride (8.02 mL, 85 mmol) was added rapidly via syringe and the cooling bath was removed. Gentle gas evolution was observed as the temperature warmed to about 10° C. The temperature continued to rise slowly to 25° C. over 45 min. Stirring was continued at ambient temperature and the reaction was monitored occasionally by TLC. After stirring overnight, some of the desired product had precipitated from solution, and TLC showed mostly the desired tri-O-acctyl derivative, with less than 10% of the di-O-acetyl intermediates remaining. The reaction was quenched by pouring the thick slurry into a stirred solution of ortho-boric acid (10.51 g, 0.17 mol, $H_3BO_3$) in deionized water (200 mL) at 25° C. Ice (60 g) was added to the resulting thin slurry, to keep the temperature below 30° C. This slurry (pH 4.5) was stirred for 15 min., then the precipitate was collected by filtration and was washed with water (2×20 mL) and methanol (2×10 mL) and was air dried to obtain 3.5 g (50% yield) of 2-fluoro-2',3',5'-tri-O-acetyladenosine as an off-white powder, mp 195°–196° C.

Example 16: 2-Fluoro-2',3',5'-tri-O-acetyladenosine

[Acetylation and Diazotization/Fluorination]

See Reaction Scheme 2; compound 12 to compound 14 to compound 15, wherein R is acetyl.

A mixture of 2-aminoadenosine (1.22 g, 4.3 mmol) and glacial acetic acid (15 mL) was warmed gently until it became homogeneous then cooled to ambient temperature. 4-Dimethylaminopyridine (26 mg, 0.2 mmol, DMAP) and acetic anhydride (1.34 mL, 14.2 mmol) were added and the mixture was stirred at ambient temperature for 4 days. Water (5 mL) was added and stirring was continued for 1 h before the residue was concentrated under vacuum. The residue was dissolved in chloroform and the chloroform solution was washed repeatedly with sat. $NaHCO_3$ until the pH was neutral. The chloroform layer was washed with sat. NaCl and dried over $MgSO_4$, then filtered and concentrated under vacuum to obtain 1.9 g of white foam. As determined by $^1$H NMR, this consisted of 2-amino-2',3',5'-tri-O-acetyladenosine (60%), 2-acetamido-2',3',5'-tri-O-acetyladenosine (30%), 2,6-bis-acetamido-9-β-D-(2',3',5'-tri-O-acetylribofuranosyl)purine (8%), and N-6-acetyl-2-amino-2',3',5'-tri-O-acetyladenosine (2%).

The above mixture (1.42 g, about 3.2 mmol), was dissolved in HF-pyridine (10 mL, about 56% HF), in a polypropylene test tube under a nitrogen atmosphere. The solution was magnetically stirred and cooled to −10° C. and tert.-butyl nitrite (0.40 mL, 3.4 mmol, 90%) was added via syringe over a 1 min period. The temperature was maintained at less the −5° C. for 15 min while gas evolution was observed, then the mixture was allowed to warm to ambient temperature over a 45 min period. The mixture was then poured over ice and the product was extracted into chloroform (3×25 mL). The combined chloroform extracts were washed sequentially with 25 mL portions of sat. Cu(II)$SO_4$, water, sat. $NaHCO_3$, and sat. NaCl. The chloroform extracts were dried over $MgSO_4$, filtered and the concentrated under vacuum to obtain 0.85 g of light brown foam which was mostly 2,6-difluoro-9-β-D-(2',3',5'-tri-O-acetylribofuranosyl)purine as determined by $^1$H NMR. This foam was dissolved in anhydrous 1,2-dimethoxyethane and anhydrous ammonia was bubbled through the solution. After stirring for 5 min at ambient temperature, a fine precipitate had formed and TLC (10:1 ethyl acetate:methanol) indicated that the difluoro compound had been consumed. The mixture was concentrated under vacuum and the residue was suspended in boiling absolute ethanol (30 mL). The solid was collected by filtration and dried under vacuum at 55 ° C. to obtain 0.61 g of the title compound. mp 195°–198° C. This material was consistent with an authentic sample by TLC, $^1$H NMR, IR and UV.

Example 17a: 2',3',5'-Tri-O-acetyl-2-fluoroadenosine

[Acylation]

See Reaction Scheme 2; compound 7 to compound 15, wherein R is acetyl.

Acetic anhydride (1.89 mL, 20 mmol) was added, with stirring, over a 5-minute period, to a solution of 2-fluoroadenosine (1.14 g, 4.0 mmol) and 4-dimethylaminopyridine (24 mg, 0.20 mmol) in anhydrous pyridine (11.4 mL). The mixture was stirred at ambient temperature for 1 hour, at which point the reaction was complete as determined by TLC (9:1 chloroform:methanol). The excess acetic anhydride was quenched by adding water (0.57 mL), and after stirring for an additional 15 minutes, the mixture was concentrated under vacuum until a thick, pasty residue was obtained. The residue was suspended in water (11 mL), and stirring was continued for 30 minutes. The resulting precipitate was collected by filtration, and was washed thoroughly with water (2×11 mL), then air-dried. This provided the title compound as a light tan powder, 1.39 g (84%), consistent, by NMR, with an authentic sample.

Example 17b: 2-Fluoro-2',3',5'-tri-O-benzoyladenosine

[Acylation]

See Reaction Scheme 2; compound 7 to compound 15, wherein R is benzoyl.

A solution of 2-fluoroadenosine (0.30 g, 1.05 mmol), and benzoic anhydride (0.713 g, 3.15 mmol) and 4-di-methylaminopyridine (6 mg) in anhydrous pyridine (5.0 mL) was stirred at ambient temperature. After 4 hours, TLC (6:4 ethyl acetate:dichloromethane) showed a single new product. The reaction was quenched by adding water (5 mL) and the resulting suspension was concentrated to dryness under vacuum. The residue was suspended in toluene and reconcentrated under vacuum. The residue was partitioned between chloroform and saturated aqueous sodium bicarbonate, and the organic layer was washed sequentially with saturated sodium bicarbonate, water, and with saturated sodium chloride solution and then dried over magnesium sulfate. The dried solution was filtered and concentrated under vacuum. The desired product was isolated from the resulting residue by silica gel chromatography, by gradient elution with dichloromethane containing 0–50% ethylacetate to obtain 0.42 g (67% yield) of the title compound as a solid. $^1$H NMR (DMSO-$d_6$, 300 MHz) δ 4.66 (dd, 1H), 4.76 (dd, 1H), 4.84 (q, 1H), 6.20 (t, 1H), 6.37 (t, 1H), 6.50 (d, 1H), 7.4–7.55 (m, 6H), 7.6–7.75 (m, 3H), 7.85–8.05 (m, 8H), 8.38 (S, 1H); FT-IR (KBr) 3350, 3188, 1729, 1642, 1602, 1267 cm$^{-1}$.

Example 18: 2',3',5'-Tri-O-acetyl-2-fluoroadenosine

[Acylation; Recovery of Partially Deacylated Byproducts]

See Reaction Scheme 1, synthesis of compound 4, from mixture of 5 and other partially acylated compounds, wherein R and R$^1$ are acetyl and X is NH$_2$.

The dark brown residue obtained by combining and concentrating both the aqueous and organic mother liquors from several selective deprotection reactions (14.5 g) was shown by TLC to contain a mixture of 2-fluoro2',3',5'-tri-O-acetyladenosine, 2',5'-di-O-acetyl-2-fluoroadenosine, 3',5'-di-O-acetyl-2-fluoroadenosine, 5'-O-acetyl-2-fluoroadenosine and other by-products from the hydroxylammonium acetate deprotection reaction, such as acetohydroxamic acid and acetone oxime. This residue was suspended in pyridine (170 mL) along with acetic anhydride (26 mL, 1.5 mL/g of residue) and 4-dimethyl-aminopyridine (DMAP, 0.17 g, 0.01 g/g of residue). The mixture was stirred at ambient temperature for 2 hours, at which time TLC (9:1 chloroform:methanol) indicated that no more of the partially O-acetylated components remained. The mixture was concentrated to about 25 mL under vacuum, nd the thick oily residue was suspended in toluene (about 50 mL) and was reconcentrated under vacuum. The residue was repeatedly suspended in water (3×50 mL), stirred vigorously, and each time the aqueous layer was decanted from the remaining pasty organic residue. This residue was dissolved in warm ethanol (about 100 mL) and the product was allowed to crystallize. The mixture was chilled to about 0° C. and the precipitate was collected by filtration and washed with ethanol (2×10 mL) and air-dried. This provided 5.53 g of the title compound as a light tan solid. This represents a 28% recovery of material based on the amount of material subjected to the selective deprotection reaction, and was suitable for reuse in that reaction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process comprising:
   subjecting guanosine to
   (a) conversion of the 6-keto group into a 6-amino group,
   (b) conversion of the 2-amino group into a 2-fiuoro group, and
   (c) conversion of the ribofuranosyl moiety to an arabinofuranosyl moiety,
   wherein said ribofuranosyl moiety is converted to an arabinofuranosyl moiety via a 3',5'-di-O-acyl-2'—OSO$_2$R$^2$ intermediate wherein each of the acyl groups have up to 12 C atoms and R$^2$ is C$_{1-4}$-perfluoroalkyl or perfluorophenyl.

2. A process according to claim 1, wherein conversion of said 2-amino group into said 2-fluoro group is completed before completion of the conversion of said 6-keto group into said 6-amino group.

3. A process according to claim 2, wherein:
   (1) guanosine is subjected to a hydroxy protection step, whereby the 2'-, 3'-, and 5'-hydroxy groups of guanosine are each converted into AcO groups, wherein Ac is an acyl group having up to 12 C atoms;
   (2) the product of (1) is subjected to halogenation, whereby the 2-amino and 6-keto groups are each converted to halogen atoms, wherein the 2-halo group is F, and the 6-halo group is a F, Cl or Br;
   (3) the product of (2) is subjected to amination, whereby the 6-halo group is replaced by an amino group;
   (4) the product of (3) is subjected to selective deacylation, whereby the 2'-AcO group is converted to a hydroxy group;
   (5) the product of (4) is subjected to sugar conversion, whereby the ribofuranosyl moiety is converted to an arabinofuranosyl moiety, wherein:
      (a) the 2'-hydroxy group is converted to 2'—OSO$_2$R$^2$ by sulfonylation to obtain said 3',5'-di-O-acyl-2'—OSO$_2$R$^2$ intermediate and
      (b) the 2'—OSO$_2$R$^2$ group of the product of (5)(a) is subjected to nucleophilic displacement to yield the arabinofuranosyl moiety; and
   (6) the resultant product of (5)(b) is subjected to deacylation, whereby AcO groups in the arabinofuranosyl moiety are converted to hydroxy groups.

4. A process according to claim 1, wherein said 6-keto group is converted into said 6-amino group before said 2-amino group is converted into said 2-fluoro group.

5. A process according to claim 4, comprising:
   (a) subjecting guanosine to amination, whereby the 6-keto group is converted to a 6-amino group;
   (b) subjecting the product of (a) to diazotization/fluorination whereby the 2-amino group is converted to 2-F, and subsequent acylation whereby 2',3',5'-hydroxy groups are converted to acyl-O groups wherein the acyl groups each have up to 12 C atoms;
   (c) subjecting the product of (b) to selective deacylation wherein 2'-O-acyl is converted to 2'-hydroxyl;
   (d) subjecting the product of (c) to sugar conversion whereby the ribofuranosyl moiety is converted to an arabinofuranosyl moiety, wherein
      (1) the 2'-hydroxyl group of the ribofuranosyl moiety is converted to 2'—$OSO_2R^2$ by sulfonylation to obtain said 3',5'-di-O-acyl-2—$OSO_2R^2$ intermediate; and
      (2) the 2'—$OSO_2R^2$ group of the product of (d)(1) is subjected to nucleophilic displacement with a carboxylate to yield the arabinofuranosyl moiety with a 2'-O-acyl group, wherein said acyl group has up to 12 carbon atoms; and
   (e) subjecting the product of (d)(2) to deacylation whereby acyl-O groups in the arabinofuranosyl moiety are converted to hydroxy groups.

6. A process according to claim 1, wherein a 3',5'-di-O-acyl-2-fluoroadenosine compound is subjected to sulfonylation via a sulfonating agent in pyridine to obtain said 3',5'-di-O-acyl-2'—$OSO_2R^2$ intermediate.

7. A process according to claim 6, wherein said sulfonating agent is a sulfonic anhydride.

8. A process according to claim 7, wherein said sulfonic anhydride is trifluoromethane sulfonic anhydride and $R^2$ is $CF_3$.

9. A process according to claim 1, wherein said acyl groups are each acetyl.

10. A process according to claim 1, wherein said 3',5'-di-O-acyl-2'—$OSO_2R^2$ intermediate is subjected to nucleophilic displacement of the —$OSO_2R^2$ group via a carboxylate ion.

11. A process according to claim 1,', wherein said 3',5'-di-O-acyl-2'—$OSO_2R^2$ intermediate is subjected to nucleophilic displacement of the —$OSO_2R^2$ group via a nitrite compound.

12. A process comprising:
   subjecting guanosine to
      (a) conversion of the 6-keto group into a 6-amino group,
      (b) conversion of the 2-amino group into a 2-fluoro group, and
      (c) conversion of the ribofuranosyl moiety to an arabinofuranosyl moiety,
   wherein a 2-aminoadenine nucleoside is subjected to diazotization/fluorination in an HF-pyridine medium to obtain an unprotected 2-fluoro intermediate and the 2'-,3'-and 5'-hydroxy groups of said 2-fluoro intermediate are subjected to acylation performed in said HF-pyridine medium of the prior diazotization/fluorination of said 2-aminoadenine nucleoside.

13. A process according to claim 12, wherein said 2-aminoadenine nucleoside possesses a ribofuranosyl moiety.

14. A process according to claim 12, wherein said 2-aminoadenine nucleoside is 2-aminoadenosine.

15. A process according to claim 12, wherein said 2-aminoadenine nucleoside possesses an arabinofuranosyl moiety.

16. A process according to claim 14, wherein said 2-aminoadenine nucleoside is 2-amino-ara-adenosine.

17. A process according to claim 12, wherein guanosine is initially subjected to amination, whereby the 6-keto group is converted to an amino group, yielding 2-aminoadenosine as said 2-aminoadenine nucleoside, which is subsequently subjected to diazotization/fluorination in said HF-pyridine medium and the resultant unprotected 2-fluoro intermediate is subjected to acylation in said HF-pyridine medium to obtain 2-fluoro-2',3',5'-tri-O-acyl-adenosine, wherein said acyl groups each have up to 12 carbon atoms.

18. A process according to claim 12, wherein, following diazotization/fluorination of said 2-aminoadenine nucleoside in HF-pyridine medium and subsequent acylation to achieve a resultant 2-fluoro-acylated-adenine nucleoside, said HF-pyridine medium is treated with a borate species to react with HF and form a fluoroborate species.

19. A process according to claim 18, wherein said 2-aminoadenine nucleoside subjected to diazotization/fluorination in HF-pyridine medium is a 2-amino-6-X-9-β-D-2',3',5'-tri-O-acyl-arabinofuranosylpurine, wherein X is Cl, Br, F, $NH_2$, or $N_3$.

20. A process according to claim 12, wherein said diazotization/fluorination is conducted in 50–70% HF-pyridine and acylation is performed by adding a carboxylic anhydride to said HF-pyridine medium.

21. A process according to claim 20, wherein said carboxylic anhydride is propionic anhydride or acetic anhydride.

22. A process according to claim 20, wherein, prior to the addition of said carboxylic anhydride, the proportion of HF in the medium is diluted by the addition of anhydrous pyridine to obtain a molar ratio of HF:pyridine of 3:1–1:1.

23. A process according to claim 12; wherein said HF-pyridine medium contains as a diazotization agent tert-butyl nitrite, sodium nitrite or potassium nitrite.

24. A process comprising:
   subjecting guanosine to
      (a) conversion of the 6-keto group into a 6-amino group,
      (b) conversion of the 2-amino group into a 2-fluoro group, and
      (c) conversion of the ribofuranosyl moiety to an arabinofuranosyl moiety,
   wherein, following conversion of said 6-keto group to a 6-amino group by amination to obtain 2-aminoadenosine, the 2'-, 3'- and 5'-hydroxy groups of 2-aminoadenosine are converted to Ac-O groups, wherein Ac is an acyl group having up to 12 C atoms, the resultant O-acyl protected compound then being subjected to fluorination of the 2-amino group.

25. A process according to claim 24, wherein said O-acyl protected compound is subjected to diazotization/fluorination in HF-pyridine medium to obtain 2-fluoro-2',3',5'-tri-O-acyladenosine, wherein said acyl groups each have up to 12 carbon atoms.

26. A process comprising:
   subjecting guanosine to
      (a) conversion of the 6-keto group into a 6-amino group,
      (b) conversion of the 2-amino group into a 2-fluoro group, and
      (c) conversion of the ribofuranosyl moiety to an arabinofuranosyl moiety,
   wherein a 2-aminoadenine nucleoside is subjected to diazotization/fluorination in an HF-pyridine medium and subsequently the HF-pyridine medium, containing a 2-fluoro-acylated-adenine nucleoside, is treated with a borate species to react with HF.

27. A process comprising:

subjecting guanosine to
  (a) conversion of the 6-keto group into a 6-amino group,
  (b) conversion of the 2-amino group into a 2-fluoro group, and
  (c) conversion of the ribofuranosyl moiety to an arabinofuranosyl moiety, wherein, prior to conversion of the ribofuranosyl moiety to an arabinofuranosyl moiety, a 2-fluoro-2',3',5'-tri-O-acyl-adenosine compound wherein the acyl groups each have up to 12 C atoms is subjected to selective deacylation whereby the 2'-O-acyl is converted to 2'-hydroxy.

28. A process for the conversion of a ribofuranosyl moiety of a 3',5'-di-O-acyl-2-fluoroadenosine compound, comprising:

subjecting a 3',5'-di-O-acyl-2-fluoroadenosine compound, wherein said acyl groups each have up to 12 C atoms, to sulfonylation in pyridine using a sulfonic anhydride to obtain a 3',5'-di-O-acyl-2—$OSO_2R^2$ intermediate wherein $R^2$ is $C_{1-4}$-perfluoralkyl or perfluorophenyl; and subsequently subjecting said intermediate to nucleophilic displacement of the —$OSO_2R^2$ group using a nitrite compound or a carboxylic species, thereby converting said ribofuranosyl moiety into an arabinofuranosyl moiety.

29. A process comprising:

subjecting 2-aminoadenosine to diazotization/fluorination in an HF-pyridine medium containing an alkyl nitrite, sodium nitrite or potassium nitrite to obtain 2-fluoroadenosine; and subjecting 2-fluoroadenosine to acylation by adding an acylating agent to said HF-pyridine medium to obtain 2-fluoro-2',3',5'-tri-O-acyl-adenosine wherein said acyl groups contain up to 12 C atoms.

30. A process according to claim 29, further comprising, after said acylation, adding a borate species to said HF-pyridine medium to react with HF.

31. A process comprising subjecting a 2-aminoadenine nucleoside to diazotization/fluorination in an HF-pyridine medium and subsequently treating the HF-pyridine medium, containing a 2-fluoro-acylated-adenine nucleoside, with a borate species to react with HF.

32. A process comprising subjecting a 2-fluoro-2',3',5'-tri-O-acyl-adenosine compound wherein the acyl groups each have up to 12 C atoms to selective deacylation whereby the 2'-O-acyl is converted to 2'-hydroxy and subsequently converting the ribofuranosyl to an arabinofuranosyl moiety.

33. A 2-fluoroadenosine compound of the formula 2-fluoro-2'—$OSO_2R^2$-3',5'-di-O-acyladenosine, wherein said acyl groups each have up to 12 carbon atoms and $R^2$ is $C_1$–$C_4$-perfluoroalkyl or perfluorophenyl.

34. A 2-fluoro-ara-adenosine compound of the formula 9-β-D-[2'-O-acyl-3',5'-O-(disiloxane-1,3-diyl)arabinofuranosyl]-2-fluoroadenine, wherein acyl is up to 12 carbon atoms and said disiloxane group is of the formula —Si(Z)$_2$—O—Si(Z)$_2$—, wherein Z is a $C_3$–$C_6$-branched alkyl, $C_3$–$C_6$-branched alkoxy, or phenyl.

* * * * *